US 6,652,537 B2

(12) United States Patent
Mercereau et al.

(10) Patent No.: US 6,652,537 B2
(45) Date of Patent: Nov. 25, 2003

(54) ARTICULATING STONE BASKET

(75) Inventors: Steve Mercereau, Conyers, GA (US); Ken Butcher, Conyers, GA (US); Brad Boetner, Covington, GA (US); Frank Bimbo, Lawrenceville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/020,797

(22) Filed: Dec. 12, 2001

(65) Prior Publication Data

US 2003/0109889 A1 Jun. 12, 2003

(51) Int. Cl.⁷ .............................................. A61B 17/22
(52) U.S. Cl. ........................ 606/127; 606/113; 606/200
(58) Field of Search ................................. 606/127, 128, 606/129, 200, 110, 113, 114, 115

(56) References Cited

U.S. PATENT DOCUMENTS

| | | | |
|---|---|---|---|
| 3,791,387 A | * | 2/1974 | Itoh ............................ 606/113 |
| 4,256,113 A | * | 3/1981 | Chamness |
| 4,326,530 A | * | 4/1982 | Fleury, Jr. |
| 4,471,777 A | | 9/1984 | McCorkle, Jr. |
| 4,741,335 A | * | 5/1988 | Okada |
| 4,807,626 A | | 2/1989 | McGirr |
| 4,997,435 A | | 3/1991 | Demeter |
| 5,064,428 A | * | 11/1991 | Cope et al. ................... 606/127 |
| 5,084,054 A | * | 1/1992 | Bencini et al. |
| 5,108,406 A | | 4/1992 | Lee |
| 5,163,942 A | * | 11/1992 | Rydell ......................... 606/113 |
| 5,190,557 A | | 3/1993 | Borodulin et al. |
| 5,201,741 A | * | 4/1993 | Dulebohn |
| 5,312,417 A | | 5/1994 | Wilk |
| 5,387,219 A | | 2/1995 | Rappe |
| 5,417,697 A | | 5/1995 | Wilk et al. |
| 5,496,330 A | | 3/1996 | Bates et al. |
| 5,522,819 A | | 6/1996 | Graves et al. |
| 5,556,376 A | | 9/1996 | Yoon |
| 5,613,973 A | | 3/1997 | Jackson et al. |
| 5,817,104 A | * | 10/1998 | Bilitz et al. .................. 606/127 |
| 5,989,266 A | * | 11/1999 | Foster ........................... 606/127 |
| 6,053,934 A | * | 4/2000 | Andrews et al. |
| 6,090,129 A | | 7/2000 | Ouchi |
| 6,096,053 A | | 8/2000 | Bates |
| 6,099,534 A | | 8/2000 | Bates et al. |
| 6,159,220 A | * | 12/2000 | Gobron et al. |
| 6,168,603 B1 | * | 1/2001 | Leslie et al. |
| 6,174,318 B1 | * | 1/2001 | Bates et al. .................. 606/127 |
| 6,280,451 B1 | | 8/2001 | Bates et al. |
| 6,494,885 B1 | * | 12/2002 | Dhindsa ....................... 606/127 |

* cited by examiner

Primary Examiner—Pedro Philogene
(74) Attorney, Agent, or Firm—Kilpatrick Stockton LLP

(57) ABSTRACT

A medical retrieval device includes a handle and a hollow sheath extending forward from the handle. A slide is attached to the handle for longitudinal movement along a path between a rearward location and a forward location. A rotary actuator having an axis of rotation generally transverse to the path of movement of the slide is mounted to the slide for rotational movement with respect thereto. A basket having at least three legs is located at a forward end of the sheath. Two adjacent basket legs are connected to a first side of the rotary actuator, and the remaining basket legs are connected to the opposite side of the rotary actuator such that rotation of the rotary actuator displaces the two legs in a first direction with respect to the sheath and displaces the remainder of the legs in a direction opposite the first direction. The basket is retracted within a forward portion of the sheath when the slide is in the rearward location, and the basket is extended forward of the forward end of the sheath when the slide is in the forward location. Thus longitudinal movement of the slide extends and retracts the basket, and rotation of the rotary actuator articulates the basket.

31 Claims, 22 Drawing Sheets

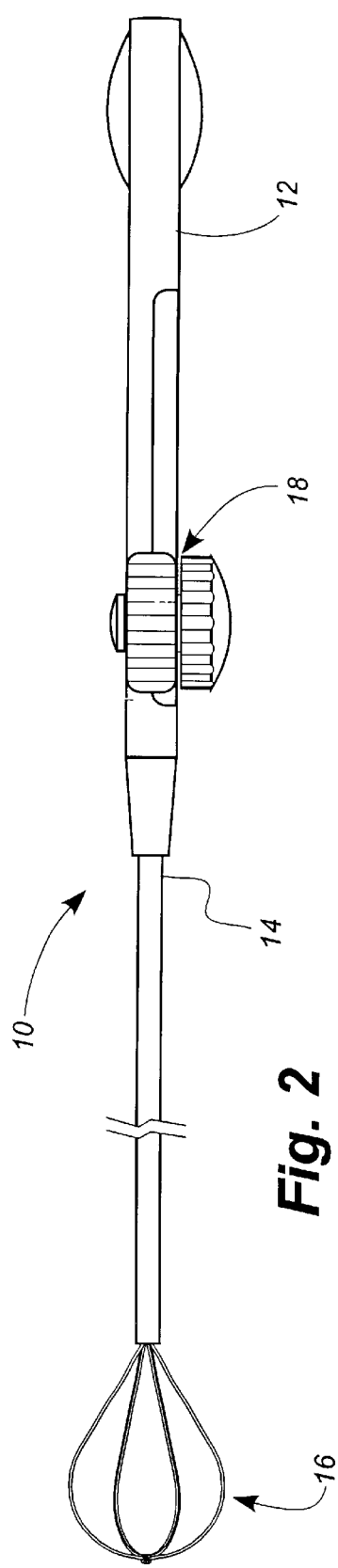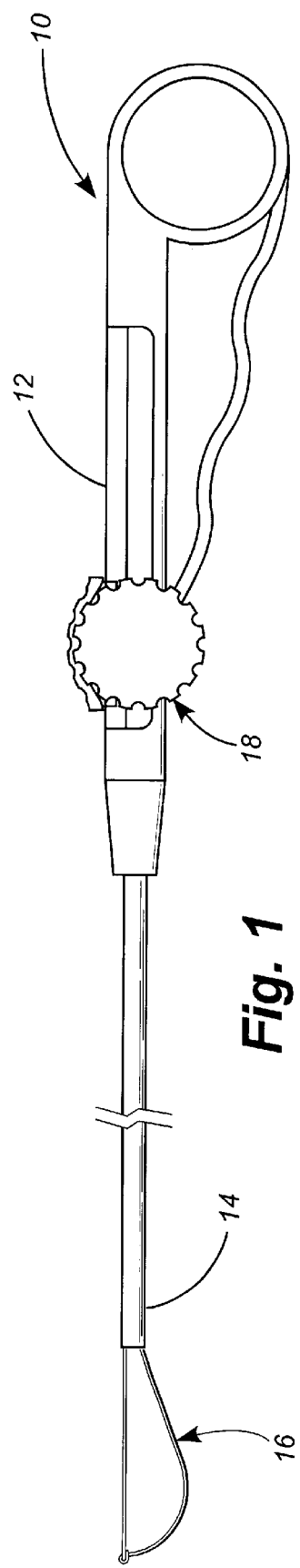

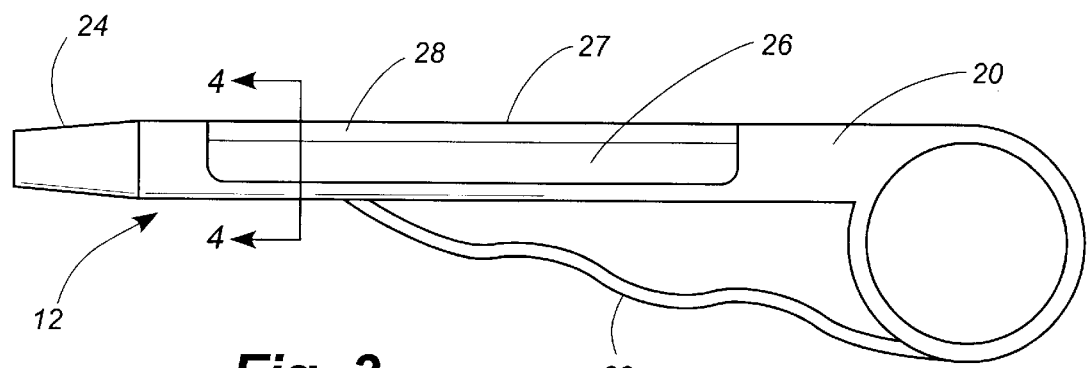
Fig. 3
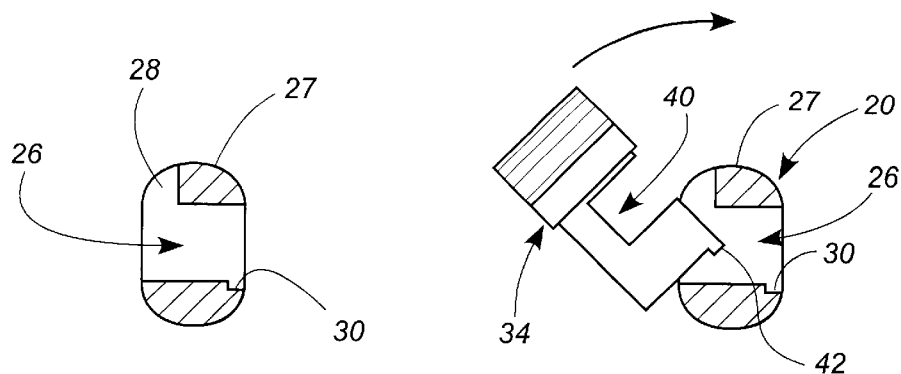
Fig. 4   Fig. 12
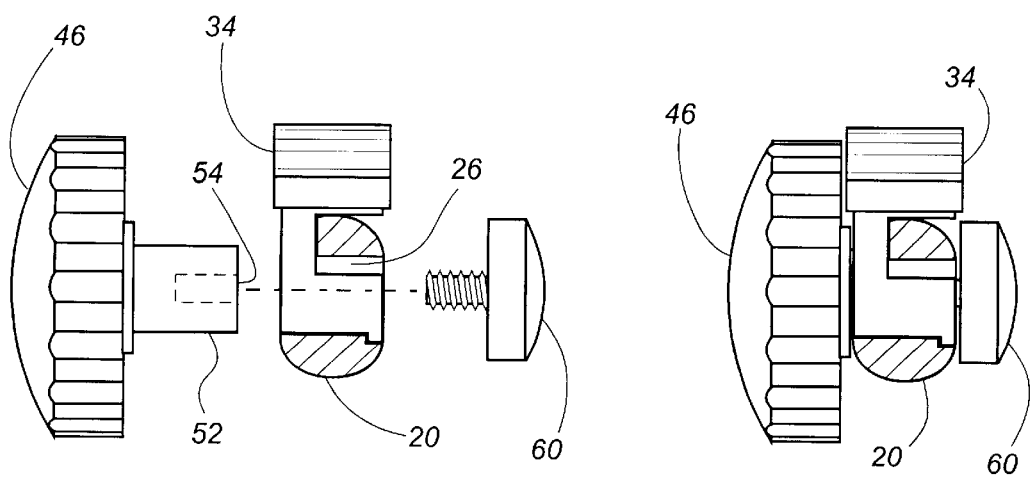
Fig. 13   Fig. 14

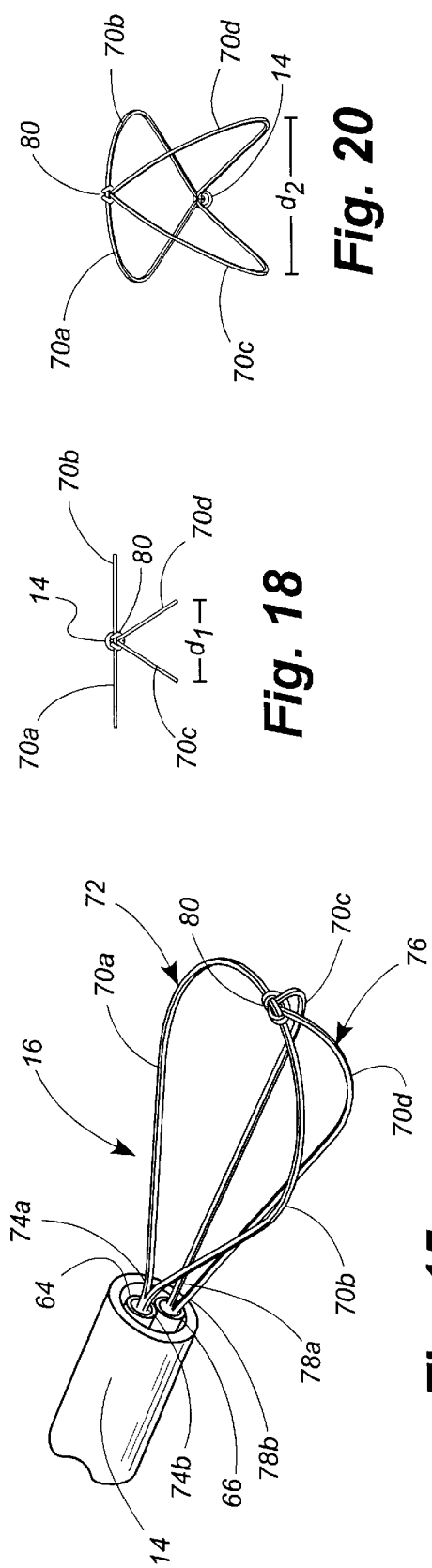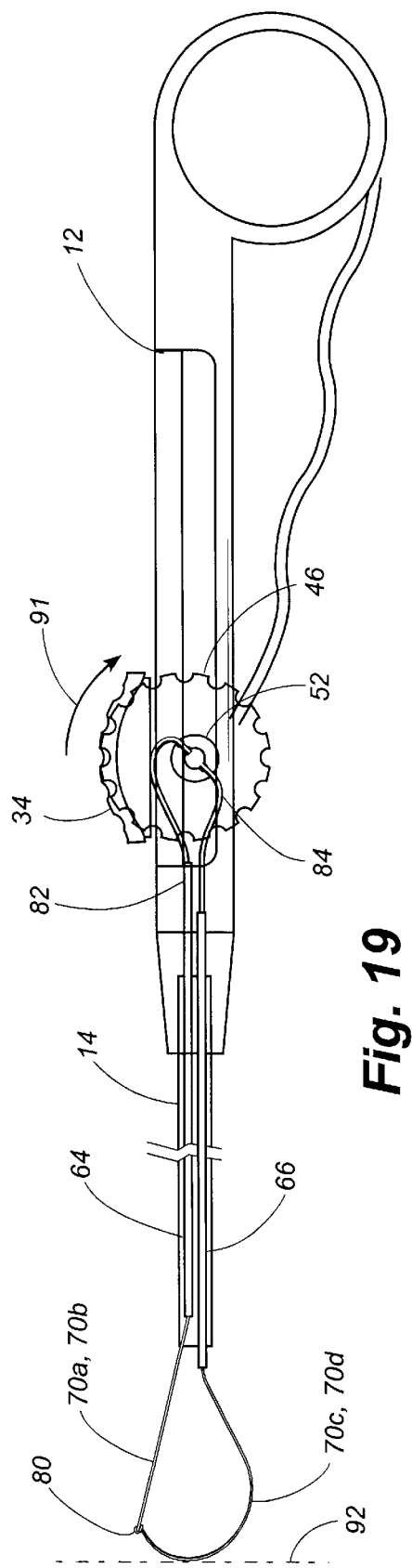

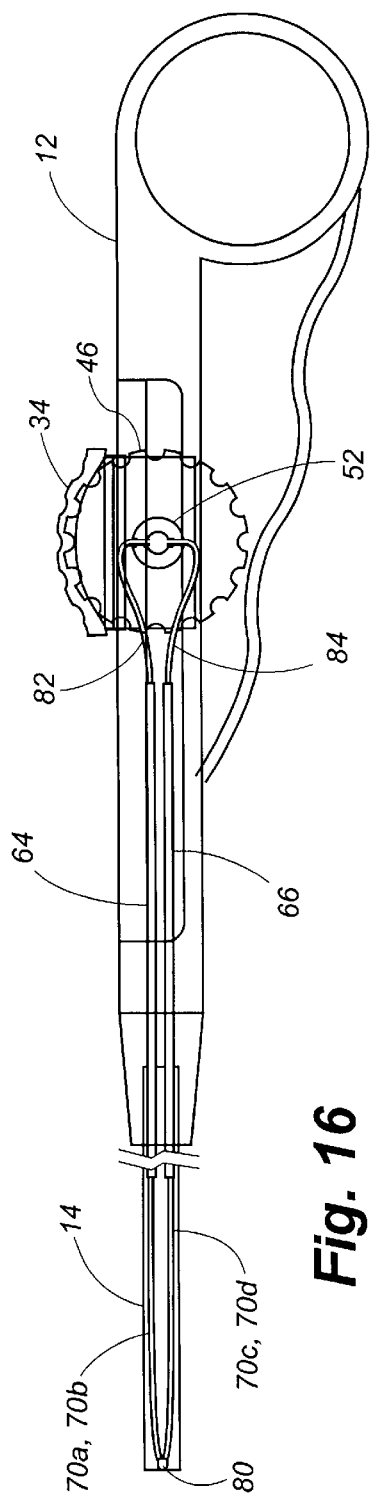
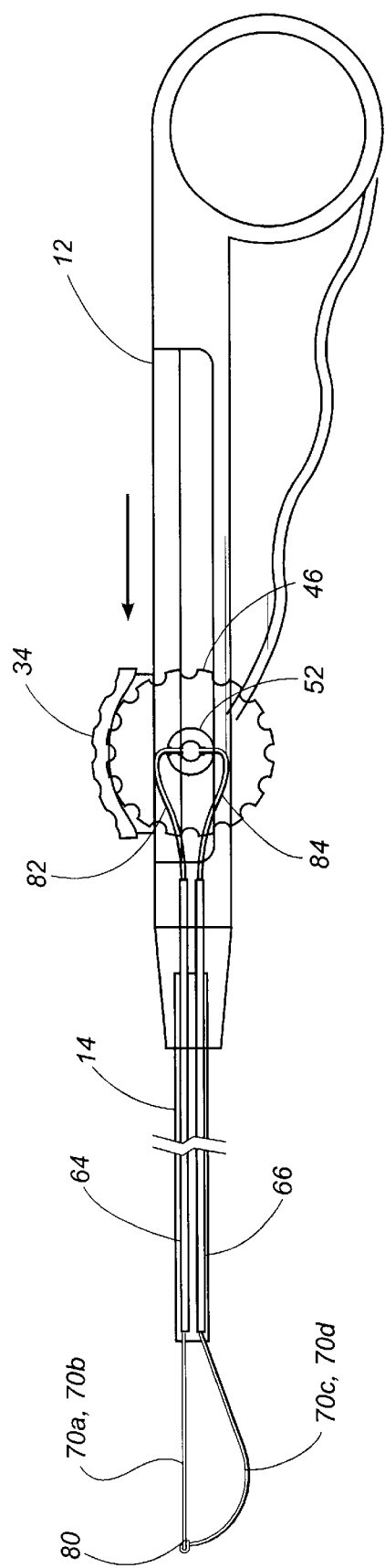
Fig. 16
Fig. 17

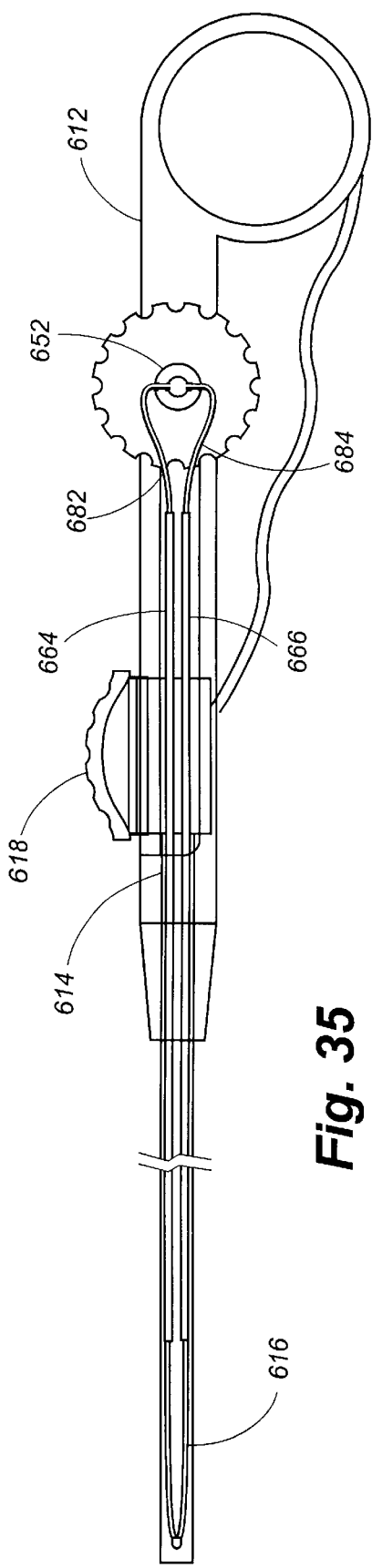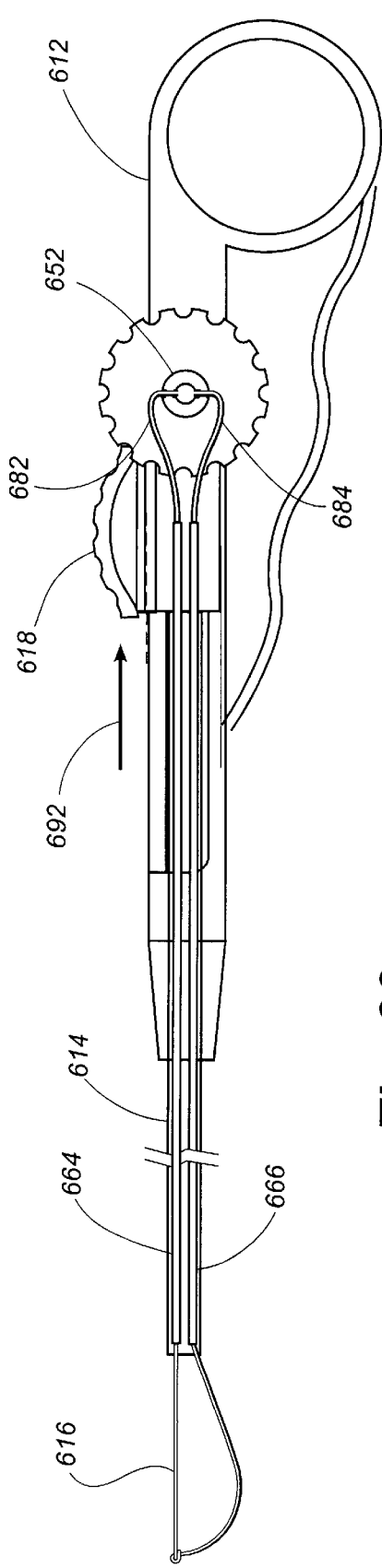

ARTICULATING STONE BASKET

TECHNICAL FIELD

The present invention relates generally to surgical retrieval instruments and relates more specifically to a surgical retriever or stone basket in which the tip can be articulated.

BACKGROUND OF THE INVENTION

Stone baskets for capturing and extracting stones from ureters are well known. Such instruments typically comprise a basket at the forward end of an elongated sheath. Wires disposed within the sheath connect the basket to a handle at the opposite end of the sheath. Various mechanisms for expanding and contracting the basket may be associated with the handle.

Today's stone baskets and graspers are being used for purposes other than simply capturing a stone in a ureter. They must also be able to reach the kidney, capture a stone, reposition it, remove it, or hold it for adjunctive treatment. Larger baskets can capture larger stones but perform poorly in capturing smaller stones. Known stone baskets cannot readily release a stone if complications arise and there is a need to exit quickly. On occasion, a physician may actually have to cut the basket wires in order to release a stone, which presents the obvious complication of having to extract the basket wires from the patient.

SUMMARY OF THE INVENTION

Stated generally, the present invention comprises a medical retrieval device having a handle. An actuator is mounted to the handle for rotational movement. A basket has at least three legs, an adjacent two of the legs being connected to a first location on the actuator radially spaced apart from its axis of rotation. The remainder of the legs are connected to a second location on the actuator radially spaced apart from the axis of rotation such that rotation of the actuator displaces the two legs in a first direction and displaces the remainder of the legs in a second direction different from the first direction. Rotation of the actuator thus articulates the basket In a disclosed embodiment the medical retrieval device has a hollow sheath attached to and extending forward from the handle. A slide is attached to the handle for longitudinal movement, and the slide is movable along a path between a rearward location and a forward location. The actuator is mounted to the slide for rotational movement. The basket is retracted within a forward portion of the sheath when the slide is in the rearward location, and the basket is extended forward of the forward end of the sheath when the slide is in the forward location. Thus longitudinal movement of the slide extends and retracts the basket, and rotation of the rotary actuator articulates the basket.

In another disclosed embodiment the sheath is attached to the slide such that longitudinal movement of the slide displaces the sheath to cover or to expose the basket.

In the disclosed embodiments the slide assembly is moved along its longitudinal path by the operator applying pressure with his thumb to a button on the top of the slide assembly. In some disclosed embodiments the rotary actuator consists of a drum mounted to the slide for rotation. A thumb wheel is operatively associated with the drum such that rotation of the wheel by the operator's thumb causes the drum to rotate to articulate the basket.

A special feature of the disclosed embodiment is that, after having grasped a stone, the basket is capable of releasing it. Thus if a physician begins to withdraw a stone and finds it is too large to pass through a physiological constriction such as the intramural ureter, or if complications arise which require rapid extraction of the stone basket, the physician can articulate the basket to spread the basket wires, thereby releasing the stone.

Objects, features, and advantages of the present invention will become apparent upon reading the following specification, when taken in conjunction with the drawings and the appended claims.

BRIEF DESCRIPTION OF THE DRAWINGS

FIG. 1 is a side view of a medical retrieval device according to a preferred embodiment of the invention.

FIG. 2 is a top view of the medical retrieval device of FIG. 1.

FIG. 3 is a side view of the handle of the medical retrieval device of FIG. 1.

FIG. 4 is a cross-sectional view taken along line 4—4 of FIG. 3.

FIG. 12 shows the assembly of the slide of FIG. 5 onto the handle of FIG. 3.

FIG. 13 shows the assembly of the thumb wheel of FIG. 9 onto the handle and slide assembly of FIG. 12.

FIG. 14 shows the assembled handle, slide, and thumb wheel of FIG. 13.

FIG. 15 is an enlarged perspective view of the basket of the medical retrieval device of FIG. 1.

FIG. 16 is a side cutaway view of the medical retrieval device of FIG. 1 with the basket in a retracted position.

FIG. 17 is a side cutaway view of the medical retrieval device of FIG. 1 with the basket in an extended position.

FIG. 18 is a front view of the basket in the extended position of FIG. 17.

FIG. 19 is a side cutaway view of the medical retrieval device of FIG. 1 with the basket in an extended and articulated position.

FIG. 20 is a front view of the basket in the extended and articulated position of FIG. 19.

FIG. 35 is a side view of an alternate embodiment of a stone basket in which the sheath is connected to the slide, showing the sheath in an extended position so as to cover the basket.

FIG. 36 is a side view of the alternate embodiment of FIG. 35 showing the sheath in a retracted position so as to expose the basket.

In FIG. 45 the movable tube is in a retracted or rearward position.

FIGS. 47–49 are perspective views showing a first method of use of the stone basket of FIG. 1 to retrieve a stone from a lumen, in which:

FIG. 47 shows the basket retracted within the forward end of the sheath;

FIG. 48 shows the basket in its deployed position to receive the stone; and

FIG. 49 shows the stone captured within the basket.

FIGS. 50–53 are perspective views showing a second method of use of the stone basket of FIG. 1 to retrieve a stone from a lumen, in which:

FIG. 50 shows the basket in its normal, extended position;

FIG. 51 shows the basket in its downwardly articulated position, open and ready to receive a stone;

FIG. 52 shows the basket in its downwardly articulated position maneuvered to position the basket around the stone; and FIG. 53 shows the basket retracted to capture the stone.

FIGS. 54 and 55 are perspective views showing a third method of use of the stone basket of FIG. 1 to retrieve a stone from a lumen, in which:

FIG. 54 shows the basket in its upwardly articulated position, open and ready to receive a stone;

FIG. 55 shows the basket in its upwardly articulated position maneuvered to position the basket around the stone.

DETAILED DESCRIPTION OF THE DISCLOSED EMBODIMENT

Figure 5:
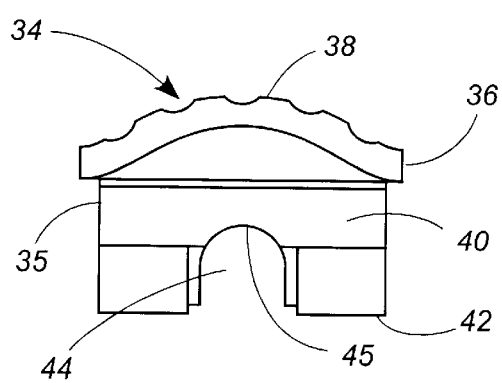
FIG. 5 is a side view of a slide of the medical retrieval device of FIG. 1.
Figure 6:
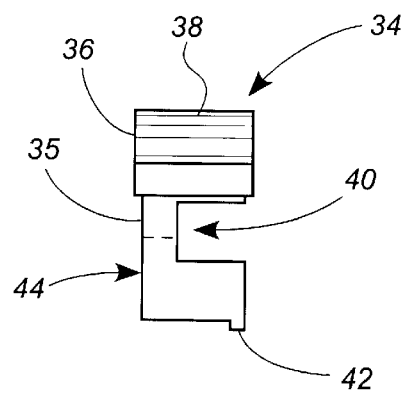
FIG. 6 is a front view of the slide of FIG. 5.
Figure 7:
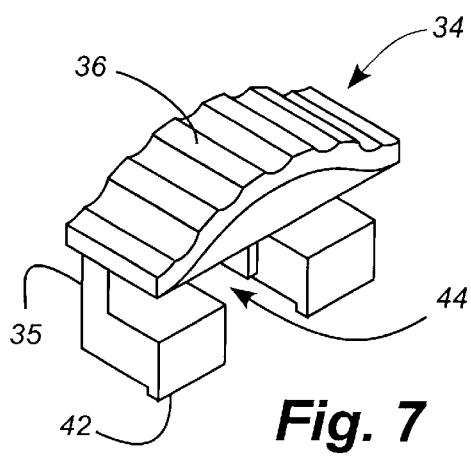
FIG. 7 is a front perspective view of the slide of FIG. 5.
Figure 8:
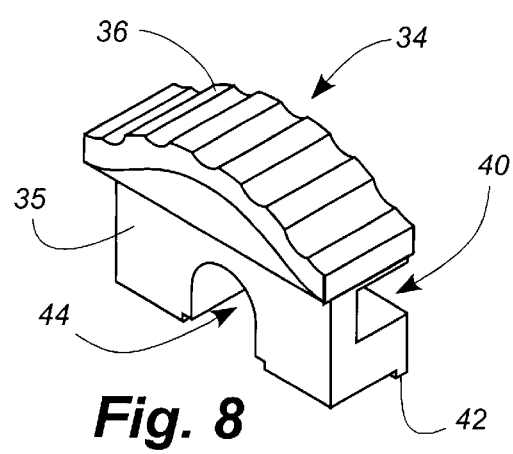
FIG. 8 is a rear perspective view of the slide of FIG. 5.

Referring now to the drawings, in which like numerals indicate like elements throughout the several views, FIGS. 1 and 2 show a stone basket 10. The stone basket 10 includes a handle 12, a sheath 14 attached to the forward end of the body, a basket 16 extending from the forward end of the sheath 14, and a slide assembly 18 slidably mounted to the body 12.

FIGS. 3 and 4 illustrate the handle 12 of the stone basket 10 in further detail. The handle 12 includes a handle body 20. A grip 22 contoured to fit the hand of the operator is formed along the lower edge of the handle body 20. A hollow nose 24 is formed at the forward end of the handle body 20. A longitudinal slot 26 extends through the handle body and communicates with the hollow nose 24. An elongated spine 27 defines the upper edge of the longitudinal slot 26. As shown in FIG. 4, an upwardly opening channel 28 is formed adjacent to the spine 27 along one lateral edge of the longitudinal slot 26. A downwardly extending groove 30 is formed along the opposite lateral edge of the longitudinal slot 26.

FIGS. 5–8 show a thumb slide 34 of the slide assembly 18. The thumb slide 34 includes a body portion 35 and a button member 36 atop the body portion 35 and adapted to receive the thumb of the operator. The button member 36 includes a ribbed upper surface 38 to minimize slippage of the operator's thumb on the button member 36. Immediately beneath the button member 36 a recess 40 is formed in a lateral edge of the body potion 35. At the lower edge of the body portion 35 along the same lateral edge in which the recess 40 is formed is a runner 42. A transverse keyway 44 having a semicircular upper edge 45 extends upward from the lower face of the body portion 35.

Figure 9:
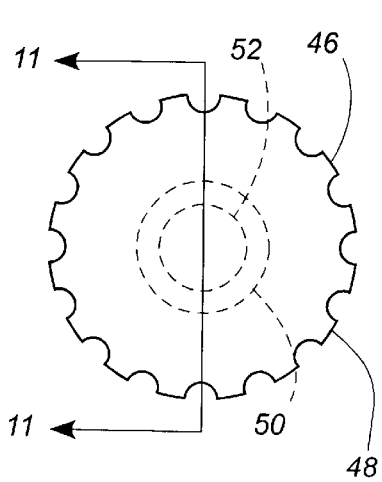
FIG. 9 is a side view of a thumb wheel of the stone basket of FIG. 1.
Figure 10:
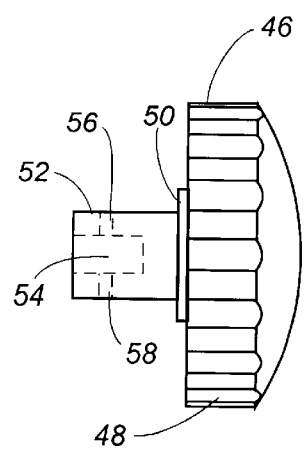
FIG. 10 is a front view of the thumb wheel of FIG. 9.
Figure 11:
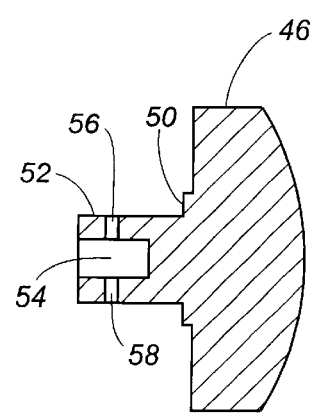
FIG. 11 is a cross-sectional view taken along line 11—11 of FIG. 9.

FIGS. 9–11 depict a thumb wheel 46 of the slide assembly 18. The thumb wheel 46 has a ribbed periphery 48, again to minimize slippage of the operator's thumb. The thumb wheel further has a raised tab 49 formed at the twelve o'clock position which provides a visual and tactile indicator to the physician as to the angular orientation of the wheel. The thumb wheel 46 has a concentric, disk-shaped boss 50 formed on its inner surface. A cylindrical drum 52 is formed concentric with the boss 50 and extends inward from the thumb wheel 46. The drum 52 is dimensioned to fit within the keyway 44 of the thumb slide 34. A threaded bore 54 is formed in the free end of the drum 52. Upper and lower radial passages 56, 58 are formed in the drum 52 and extend from the threaded bore 54 radially outward to the upper and lower edges, respectively, of the drum.

Assembly of the thumb slide 34 and thumb wheel 46 onto the handle body 20 is illustrated in FIGS. 12–14. Referring first to FIG. 12, the thumb slide 34 is angled so that the lower end of the thumb slide can be inserted through the longitudinal slot 26 from the side of the handle body 20 opposite the downwardly extending groove 30. The thumb slide 34 is then pivoted into its upright position, with the spine 27 of the handle body 20 fitting within the recess 40 of the thumb slide. The runner 42 on the lower lateral edge of the thumb slide 34 rides in the groove 30 in the lateral edge of the longitudinal slot 26.

Referring now to FIGS. 13 and 14, with the thumb slide 34 slidably mounted within the longitudinal slot 26 in the handle 12, the drum 52 of the thumb wheel 46 is inserted through the keyway 44 in the thumb slide. To retain the thumb wheel 46 on the thumb slide 34, the threaded shank of a screw 60 is inserted into the threaded bore 54 of the thumb wheel. The thumb slide 34 is now slidably mounted to the handle 12, and the thumb wheel 46 is rotatably mounted to the thumb slide.

FIG. 15 is an enlarged view of the basket 16 and the forward end of the sheath 14. A pair of elongated tubes 64, 66 are slidably disposed within the sheath 14. The basket 16 includes a pair of upper legs 70a, 70b and a pair of lower legs 70c, 70d. The upper legs 70a, 70b are formed from a single loop 72 of a flat cross-sectional wire. The ends 74a, 74b of the loop 72, and thus the rearward ends of the legs 70a, 70b, are attached to the upper elongated tube 64 which is telescopically disposed within the sheath 14.

Similarly, the lower two legs 70c, 70d of the basket 16 are formed from a single loop 76 of round cross-sectional wire. The ends 78a, 78b of the loop 76, and thus the rearward ends of the legs 70c, 70d, are attached to the lower elongated tube 66 which is telescopically disposed within the sheath 14. The basket legs 70a–70d of the disclosed embodiment are secured to the tubes 64, 66 by inserting the rearward ends of the legs into their respective tubes and then crimping the tube ends. However, it will be appreciated that other means for mounting the basket legs to the tubes may be employed, including adhesives, welding, and the like.

The upper and lower loops 72, 76 of the basket 16 are joined at their forward central portions at a junction 80. In the embodiment of FIG. 15, the junction is formed by tying the two loops 72, 76 together. The upper loop 72 is formed, and then the lower loop 76 is tied over it using a larkshead knot.

FIGS. 16–20 illustrate further details of the stone basket 10 and its operation. The elongated tubes 64, 66 are telescopically disposed within the sheath 14 of the stone basket 10. The basket 16 is mounted to the forward ends of the tubes 64, 66. The rearward ends of the tubes 64, 66 are operatively connected to the thumb wheel 46 as follows. An upper cable 82 has its forward end connected to the rearward end of the upper tube 64, such as by crimping, adhering, welding, or otherwise bonding the cable to the tube. Similarly, a lower cable 84 has its forward end connected to the rearward end of the lower tube 66. The forward ends of the cables 82, 84 are inserted into the upper and lower radial passages 56, 58 on the drum 52 of the thumb wheel and secured by adhering, welding, or otherwise bonding the cable ends within the passages. In the alternative, the ends of the cables 82, 84 can be inserted through the passages and into the bore 54, where subsequent insertion of the screw 60 will clamp the cable ends.

Operation of the stone basket 10 will now be described with reference to FIGS. 16–20. In FIG. 16, the slide assembly 18 is in a rearward position with respect to the handle 12, and the basket 16 is retracted within the forward end of the sheath 14. When the slide assembly 18 is advanced as shown in FIG. 17, the tubes 64, 66 are telescopically advanced within the sheath 14, extending the basket legs 70a–70d from the forward end of the sheath. The basket legs 70 are preferably formed from a shape memory metal such as nitinol, such that the legs, once freed from the confines of the sheath 14, spring outward into their predetermined configurations.

FIG. 18 is a front view of the basket 16 when extended as shown in FIG. 17. The basket 16 is shaped like a spoon, with the upper legs 70a, 70b forming the upper edge of the spoon and the lower legs 70c, 70d forming the bowl. In its normal open configuration, the lower legs 70c, 70d are separated by a distance $d_1$.

In FIG. 19 the thumb wheel 46 is rotated rearward, in the direction indicated by the arrow 91. This rotation exerts a tension on the upper cable 74, drawing the upper tube 64 rearward. Simultaneously the lower cable 76 is advanced. The cables 74, 76 have sufficient stiffness that the lower tube 66 is advanced. Thus the tubes 64, 66 move in reciprocal directions. This retraction of the upper tube 64 and extension of the lower tube 66 causes the upper basket legs 70a, 70b to retract and the lower basket legs 70c, 70d to extend, thus articulating the basket 16 upward.

Referring to FIGS. 19 and 20, articulation of the basket 16 causes several advantageous effects. First, as can be seen in FIG. 19, the junction 80 is displaced rearward of a plane 92 defined by the forward edge of the basket 16. Thus if a stone is lodged against a wall perpendicular to the longitudinal axis of the device 10, the junction 80 does not prevent the basket 16 from being advanced right up against the wall to capture the stone. Second, as can be seen in FIG. 20, in the basket's articulated configuration the lower legs 70c, 70d are spread apart by a distance $d_2$, which is larger than distance $d_1$ of FIG. 18. Thus articulation of the basket 16 causes the two lower legs 70c, 70d to spread apart in clamshell fashion, thus making it easier to maneuver the basket around a stone.

The arrangement by which movement of one of the tubes 64, 66 causes an equal-but-opposite movement of the other tube provides the advantage that rotation of the thumb wheel 46 by a given amount results in twice the effective "throw." Thus less movement of the thumb wheel 46 is required to effect the same range of articulation. The throw of the device is also determined by the diameter of the drum 52.

While the foregoing embodiment employs a pair of tubes 64, 66 telescopically disposed within the sheath 14 to facilitate coupling the basket legs 70a–70d to the drum 52 of the thumb wheel 46, it will be appreciated that the basket wires may instead be made sufficiently long to extend the length of the sheath and couple directly to the drum. In the alternative, it will be appreciated that more than two tubes can be used to couple the basket legs 70a–70d to the drum 52 of the thumb wheel 46. For example, each leg 70a–70d can be attached to its own tube, with more than one tube attached within a given radial passage of the drum 52.

Further, while the foregoing embodiment 10 provides a thumb wheel 46 which the operator turns to rotate the drum 52 to articulate the basket 16, it will be appreciated that the thumb wheel is not essential to the operation of the device. For example, a lever coupled to the drum could be used in lieu of the thumb wheel, or an electric motor could be arranged to rotate the drum when actuated. Similarly, while the slide assembly 18 of the embodiment 10 is manually advanced and retracted along its path of movement on the handle 12 by the operator's finger, it will be appreciated that alternate arrangements for longitudinally displacing the slide assembly with respect to the handle may be used, including an electric motor or a wheel and pulley.

Figure 21:
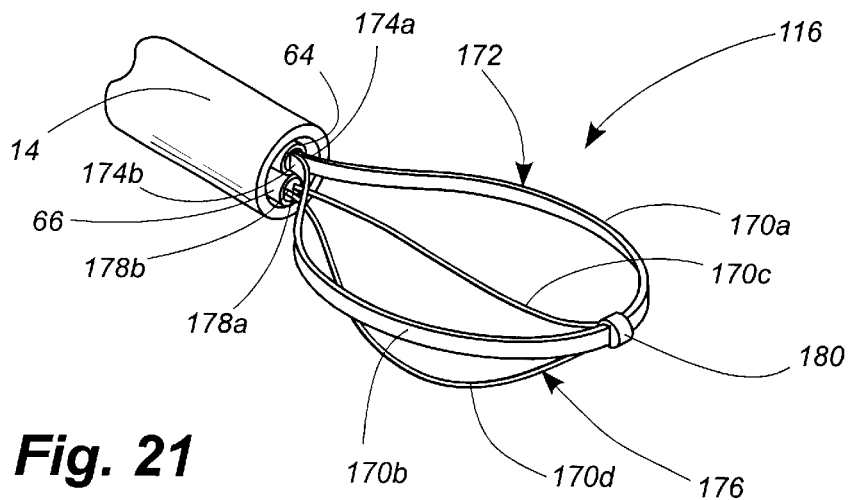
FIG. 21 is an enlarged perspective view of a first alternate embodiment of a basket for use with the actuation mechanism of the device of FIG. 1.
Figure 22:
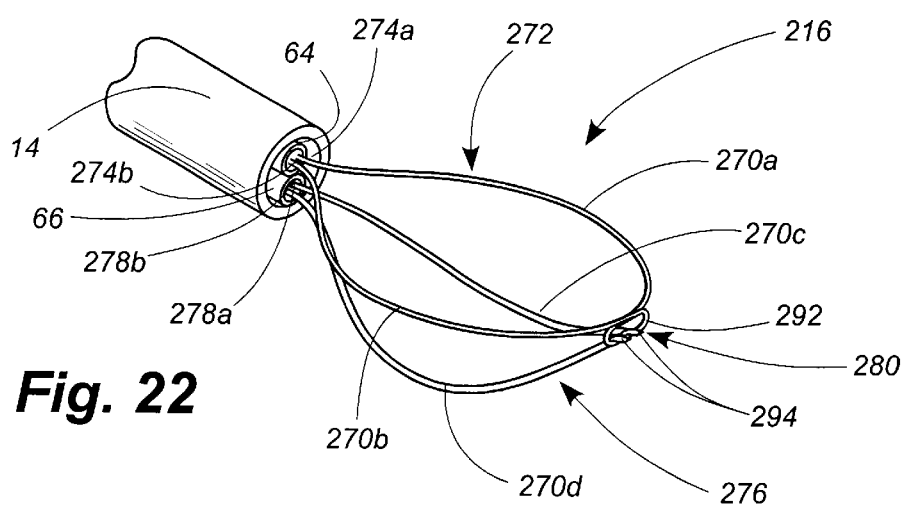
FIG. 22 is an enlarged perspective view of a second alternate embodiment of a basket for use with the actuation mechanism of the device of FIG. 1.
Figure 23:
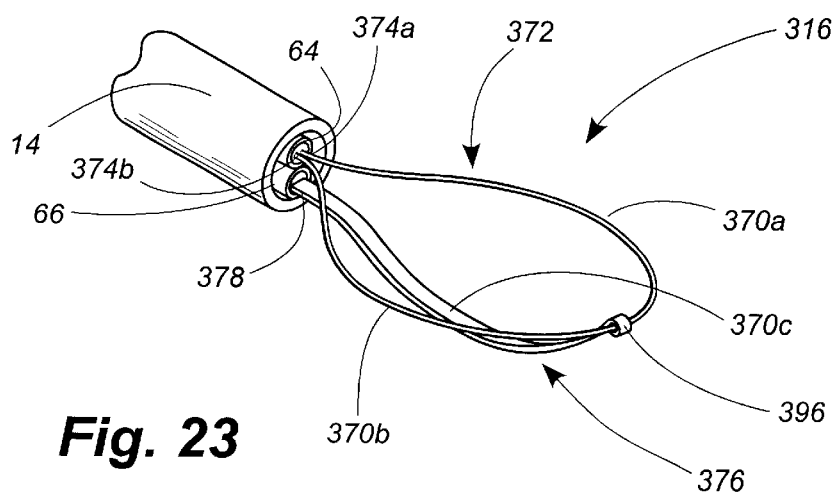
FIG. 23 is an enlarged perspective view of a third alternate embodiment of a basket for use with the actuation mechanism of the device of FIG. 1.

FIGS. 21–23 show alternate embodiments of baskets which can be used with the actuation mechanism hereinbefore described. Referring first to FIG. 21, a basket 116 includes basket legs 170a–170d. The upper legs 170a, 170b of the basket 116 are formed from a single loop 172 of a flat cross-sectional wire. The ends 174a, 174b of the loop 172, and thus the rearward ends of the legs 170a, 170b, are attached to the upper elongated tube 64 which is telescopically disposed within the sheath 14.

Similarly, the lower two legs 170c, 170d of the basket 116 are formed from a single loop 176 of round cross-sectional wire. The ends 178a, 178b of the loop 176, and thus the rearward ends of the legs 170c, 170d, are attached to the lower elongated tube 66 which is telescopically disposed within the sheath 14.

The upper and lower loops 172, 176 of the basket 116 are joined at their forward central portions by a fastener 180. The fastener 190 can be a ring through which the upper and lower loops 172, 176 are passed before attaching the loop ends 174a, 174b, 178a, 178b to their respective tubes 64, 66.

Referring next to FIG. 21, a basket 216 includes two upper legs 270a, 270b formed from a single loop 272 of a round cross-sectional wire. The ends 274a, 274b of the loop 272, and thus the rearward ends of the legs 270a, 270b, are attached to the upper elongated tube 64 which is telescopically disposed within the sheath 14.

Similarly, the lower two legs 270c, 270d of the basket 116 are formed from a single loop 276 of flat cross-sectional wire. The ends 278a, 278b of the loop 276, and thus the rearward ends of the legs 270c, 270d, are attached to the lower elongated tube 66 which is telescopically disposed within the sheath 14.

The upper and lower loops 272, 276 of the basket 216 are joined at their forward central portions at a junction 280 without use of a separate fastener. The upper loop 272 is bent at its forward end to form an eye 292. Several turns 294 of the lower loop 276 wrap through this eye 292.

Another basket 316 is disclosed in FIG. 23. The two upper legs 370a, 370b of the basket 316 are formed from a single loop 372 of a round cross-sectional wire. Both ends 374a, 374b of the upper loop 372 are attached to the upper tube 64. The basket 316 includes only one lower leg 370c, which is formed from a wire having a flat cross-section. The rearward end 378 of the lower leg 370c is attached to the lower tube 66. The forward end of the lower leg 370c is bent to form a hook 398 which captures the forward central portion of the upper loop 372.

It will be understood that the baskets 16, 116, 216, and 316 are disclosed by way of example, and that the actuating mechanism of the device 10 is not limited to use with these particular basket configurations but rather can be used with a wide variety of basket configurations.

In the device 10 described above, the elongated tubes 64, 66 are attached by cables 74, 76 to the circumference of the drum 52. FIGS. 24–31 show alternate embodiments for coupling the tubes to the drum wherein the elongated tubes 64, 66 are attached to a lateral face of a drum and reciprocate as the drum is rotated.

Figure 24:
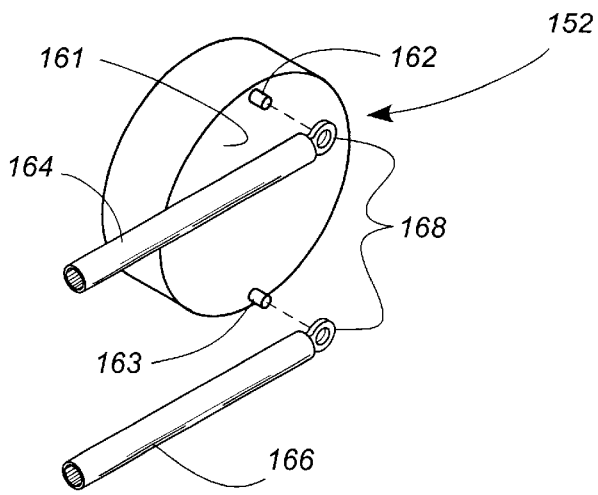
FIG. 24 is an exploded perspective view of a first alternate embodiment of an articulation drive arrangement.
Figure 25:
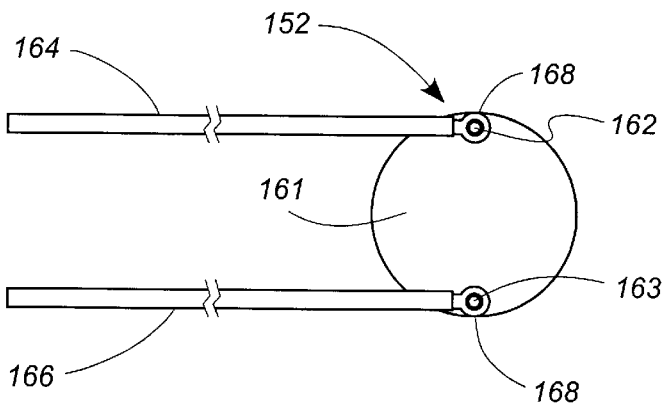
FIG. 25 is an assembled side view of the drive arrangement of FIG. 24.
Figure 26:
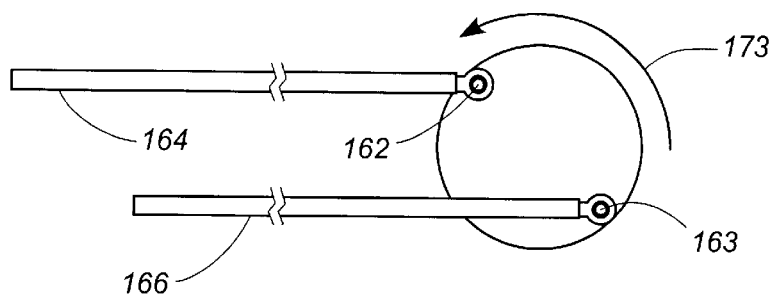
FIG. 26 is a side view showing the drive arrangement of FIG. 24 actuated in a first direction.
Figure 27:
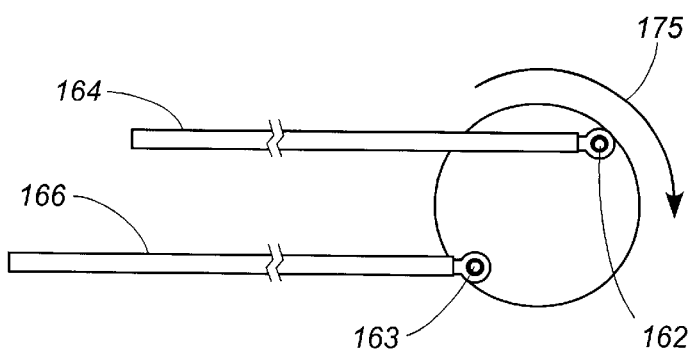
FIG. 27 is a side view showing the drive arrangement of FIG. 24 actuated in a second direction.

Referring first to FIGS. 24 and 25, the drum 152 has a lateral face 161. Upper and lower pins 162, 163 project outward from the lateral face 161 of the drum 152. Elongated tubes 164, 166 have hooks or eyelets 168 formed at their rearward ends which engage the pins 162, 163 on the lateral face 161 of the drum 152. As the drum 152 rotates in a counterclockwise direction as shown by the arrow 173 in FIG. 26, the upper pin 162 on the drum rotates toward the left, and the upper tube 164 coupled to the pin 162 is displaced forward. Simultaneously, the lower pin 163 on the drum 152 rotates toward the right, displacing the lower tube 166 rearward. If the drum 152 is rotated in a clockwise direction as shown by the arrow 175 in FIG. 27, the upper pin 162 on the drum rotates toward the right, and the upper tube 164 coupled to the pin 162 is withdrawn. Simultaneously, the lower pin 163 on the drum 152 rotates toward the left, advancing the lower tube 166.

Figure 28:
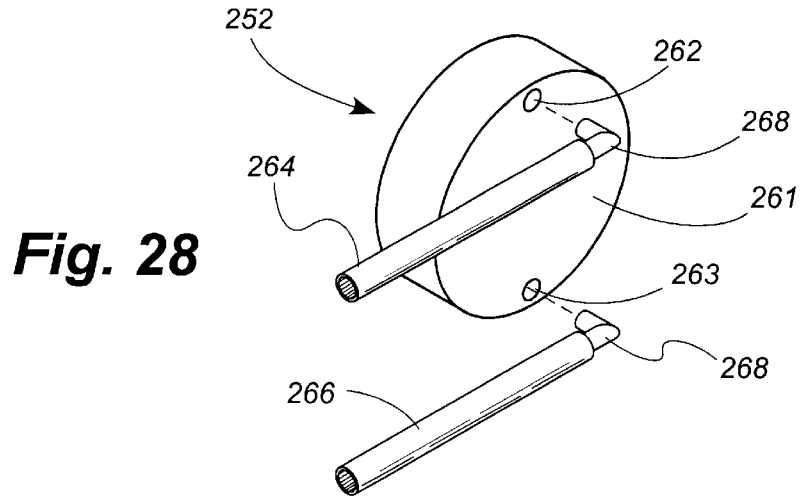
FIG. 28 is an exploded perspective view of a second alternate embodiment of an articulation drive arrangement.
Figure 29:
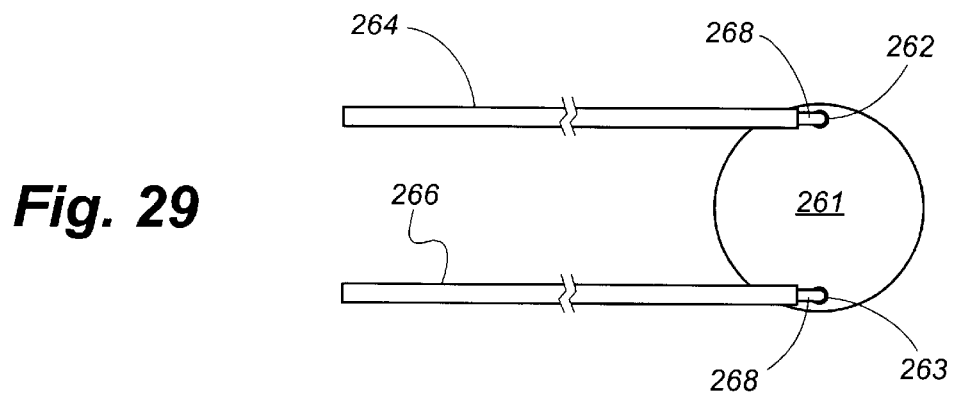
FIG. 29 is an assembled side view of the drive arrangement of FIG. 28.
Figure 30:
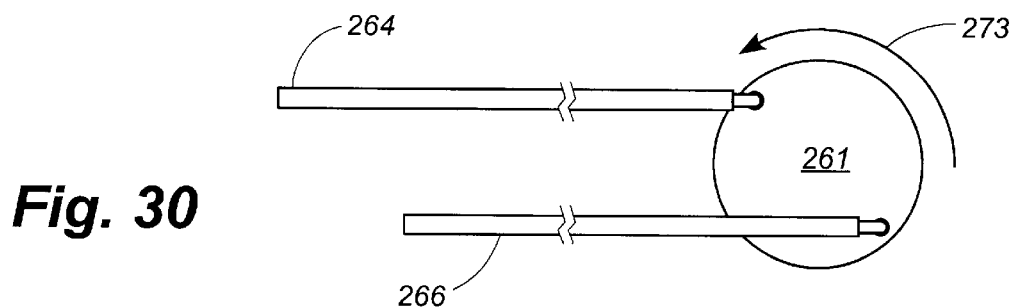
FIG. 30 is a side view showing the drive arrangement of FIG. 28 actuated in a first direction.
Figure 31:
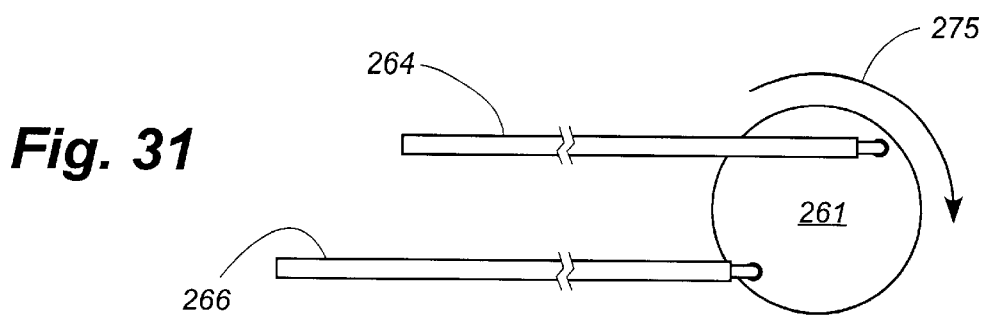
FIG. 31 is a side view showing the drive arrangement of FIG. 28 actuated in a second direction.

FIGS. 28–31 portray a similar arrangement which differs in the manner in which the tubes are coupled to the drum. Referring first to FIGS. 28 and 29, a drum 252 has a lateral face 261. Upper and lower holes 262, 263 are formed in the lateral face 261 of the drum 252. Elongated tubes 264, 266 have lateral arms 268 formed at their rearward ends which engage the holes 262, 263 on the lateral face 261 of the drum 252. As the drum 252 rotates in a counterclockwise direction as seen in FIG. 30, the upper hole 262 of the drum rotates toward the left, displacing the upper tube 264 forward. Simultaneously, the lower hole 263 of the drum 252 rotates toward the right, and the lower tube 166 coupled to the hole 263 is pulled rearward. When the drum 252 is rotated in a clockwise direction as seen in FIG. 31, the upper hole 262 of the drum rotates toward the right, and the lower hole 263 of the drum 252 rotates toward the left, retracting the upper tube 264 and advancing the lower tube 266.

Figure 32:
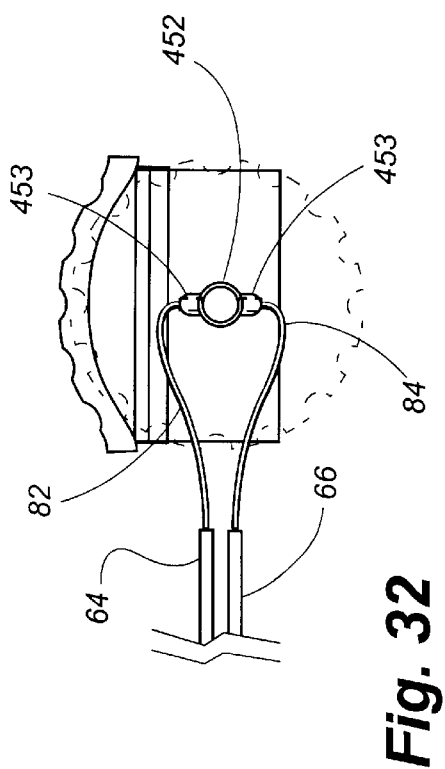
FIG. 32 is a side view of an alternate embodiment of a rotary actuator which comprises radial arms instead of a rotary drum.

Whether the elongated tubes are attached to the cylindrical wall of the drum or to a lateral face of the drum, the common feature is that the tubes are coupled to the drum at locations which are radially offset from the axis of rotation of the drum so as to be linearly displaced as the drum is rotated. Other well-known mechanical expedients for converting rotational motion into linear motion can also be substituted. For example, instead of using a drum, the tubes 64, 66 can be coupled as shown in FIG. 32 to a rotatably mounted actuator 452. The cables 74, 76 which link the tubes to the actuator 452 are fastened to the ends of radial arms 453 at locations which are radially offset from the axis of rotation of the actuator. Henceforth, for purposes of this application an element which is rotatably mounted to the device and which includes structure radially offset from its axis of rotation to which the basket wires are linked will be referred to as a "rotary actuator."

Figure 34:
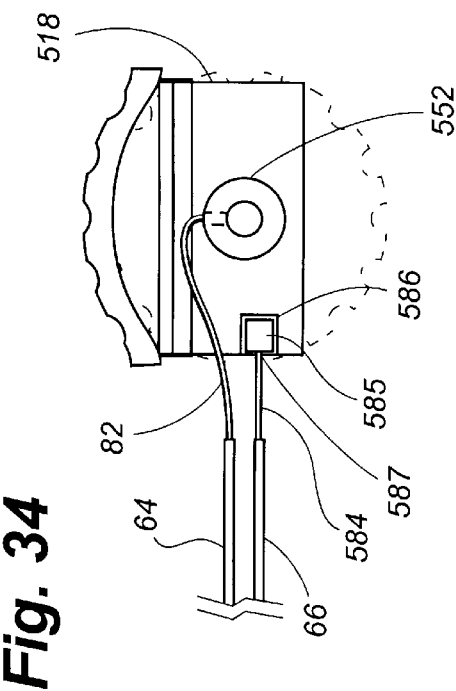
FIG. 34 is an enlarged side view of the slide and rotary actuator of the embodiment of FIG. 33.
Figure 33:
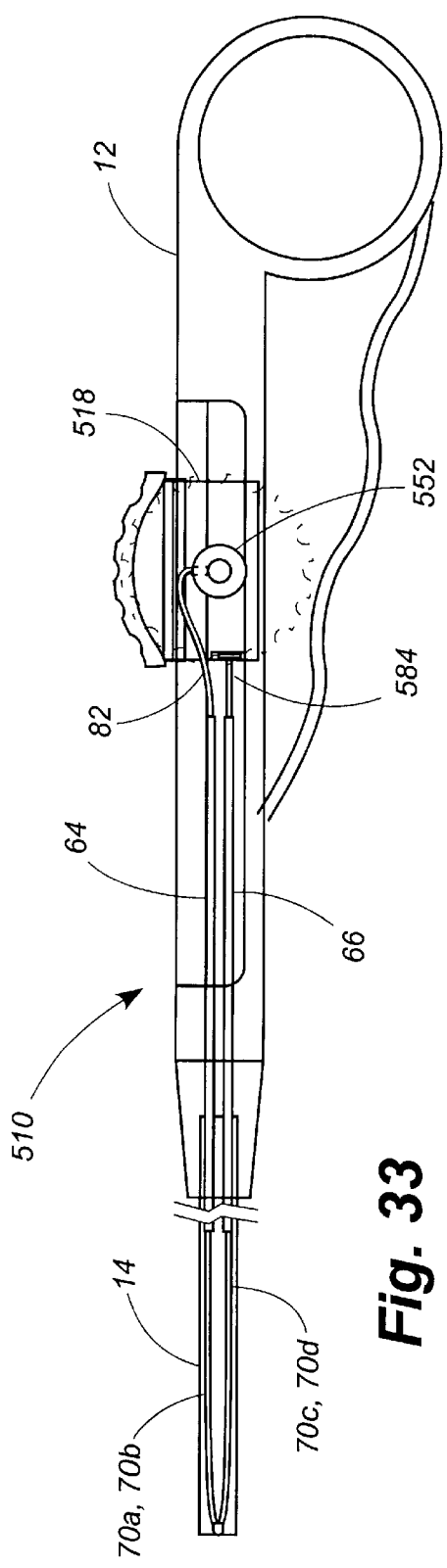
FIG. 33 side view of an alternate embodiment of a stone basket in which only one set of basket arms is articulated.

As will be appreciated, in the embodiments 10, 110, 210, and 310 described above, the motion of the basket legs is dependent, that is, movement of one basket leg is necessarily accompanied by movement of all of the other legs, either in the same direction or in an opposite direction. Stated differently, in the embodiments 10, 110, 210, and 310 it is not possible to move any leg of the basket independently of the other legs. FIGS. 33 and 34 illustrate an alternate embodiment of a stone basket 510 in which independent movement is possible of one or more of the basket legs with respect to the other legs. In the embodiment 510 only one set of basket legs is articulated. The upper tube 64 to which the upper basket legs 70a, 70b are attached is connected to a location on the periphery of a drum 552 by means of a cable 82, in the same manner previously explained. However, the lower tube 66 to which the lower legs 70c, 70d are connected is attached to the front of the slide 518 by means of a cable 584. In FIGS. 31 and 32 the cable 584 has a ferrule 585 at its free end which fits into a cooperating recess 586 in the lateral edge of the slide 518, with the cable being received through a narrow slot 587 in the front wall of the slide. Thus longitudinally advancing and retracting the slide 518 extends and retracts the basket 16, and rotating the drum 552 extends or retracts the upper legs 70a, 70b of the basket to effect articulation.

Referring now to FIGS. 35 and 36, still another embodiment 610 of a medical retrieval device includes a handle 612, a sheath 614, a basket 616, and a slide 618. As in previous embodiments the slide 618 is mounted to the handle 612 for longitudinal movement. In contrast to previously described embodiments, however, the sheath 614 is not fixedly mounted to the handle 612 but instead is mounted to the slide 618 for longitudinal movement with respect to the handle. In addition, a rotary actuator 652 is mounted to the handle 612 at a point rearward of the path of movement of the slide 618 and does not move with the slide. The tubes 664, 666 extend through the sheath 614 and through a longitudinal opening in the slide 616. Cables 682, 684 connect the rearward ends of the tubes 664, 666 to the rotary actuator 652.

In the embodiment 610, when the slide 618 is in its forward position as shown in FIG. 35, the basket 616 is covered. The basket 616 is deployed by retracting the slide 618 in the direction indicated by the arrow 692 to expose the basket, as shown in FIG. 36. Advancing the slide 618 covers the basket 616 or, if a stone has been maneuvered into the basket, tightens the basket around the stone to enable it to be withdrawn from the patient. As in previous embodiments, rotating the actuator 652 advances one of the tubes 664, 666 and retracts the other, thereby articulating the basket 616.

FIGS. 37–44 illustrate another alternate embodiment of a medical retrieval device 710 according to the present invention. The embodiment 710 is characterized by the use of linear actuators to articulate a basket, instead of the rotary actuators used in the embodiments previously described.

Figure 37:
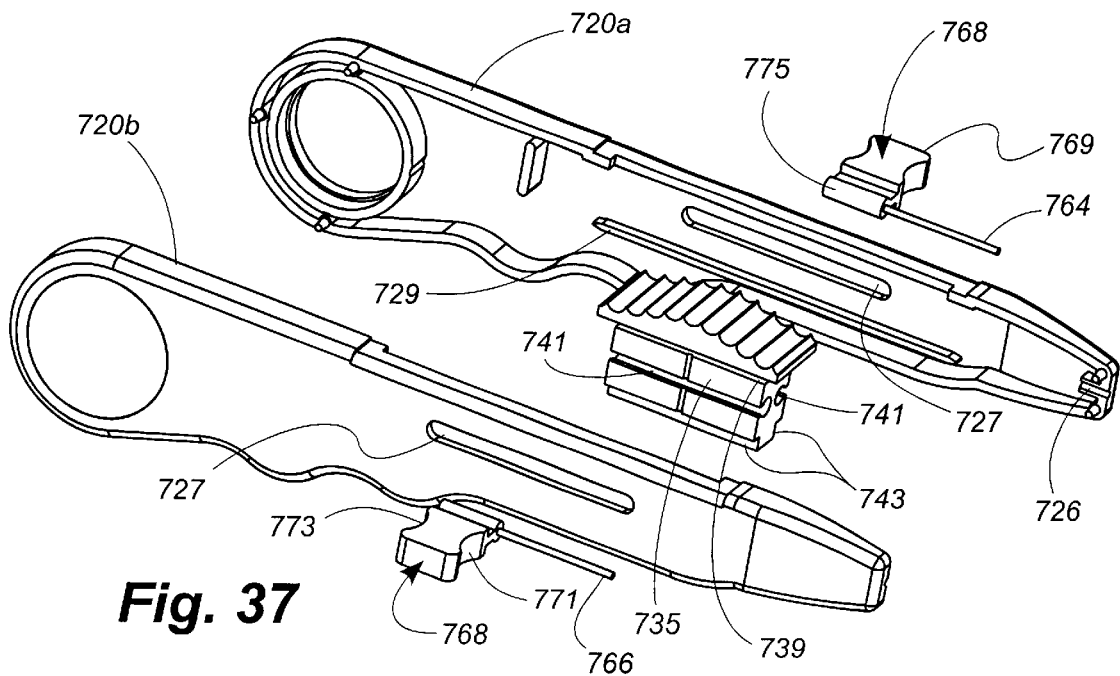
FIG. 37 is an exploded perspective view of an alternate embodiment of a medical retrieval device which employs linear actuators to articulate the basket.
Figure 38:
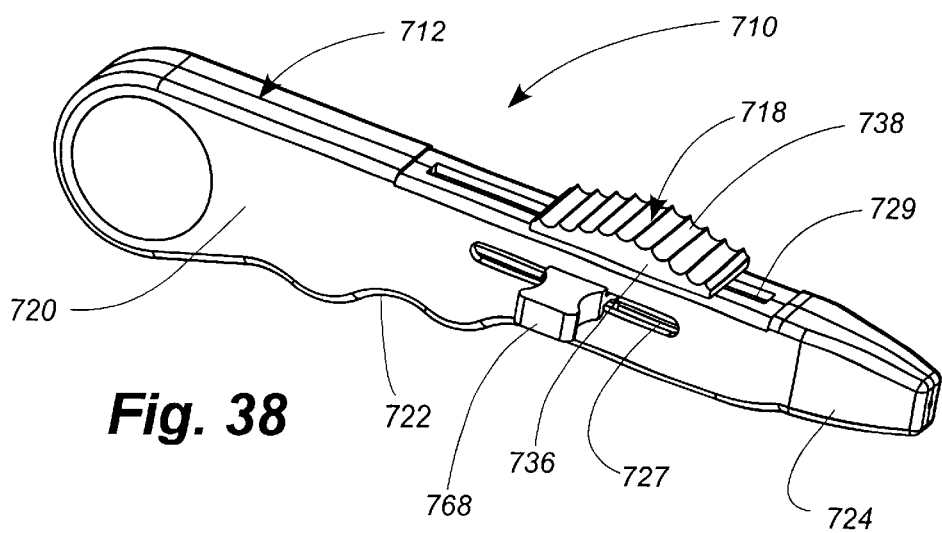
FIG. 38 is an assembled perspective view of the medical retrieval device of FIG. 37.
Figure 39:
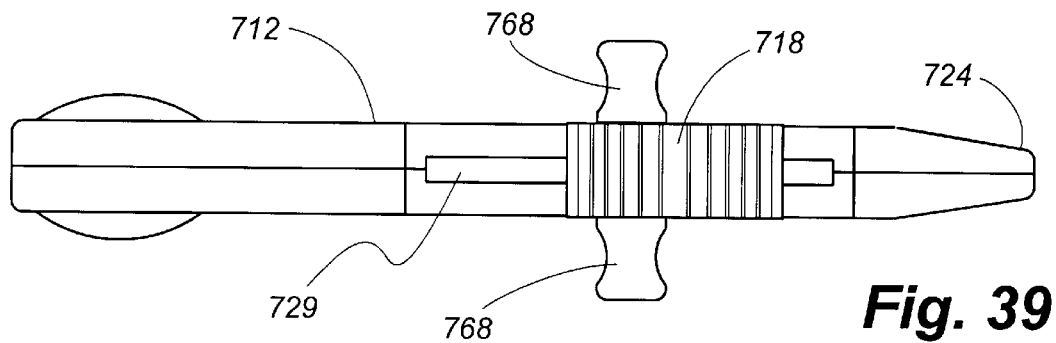
FIG. 39 is a top view of the medical retrieval device of FIG. 37.
Figure 40:
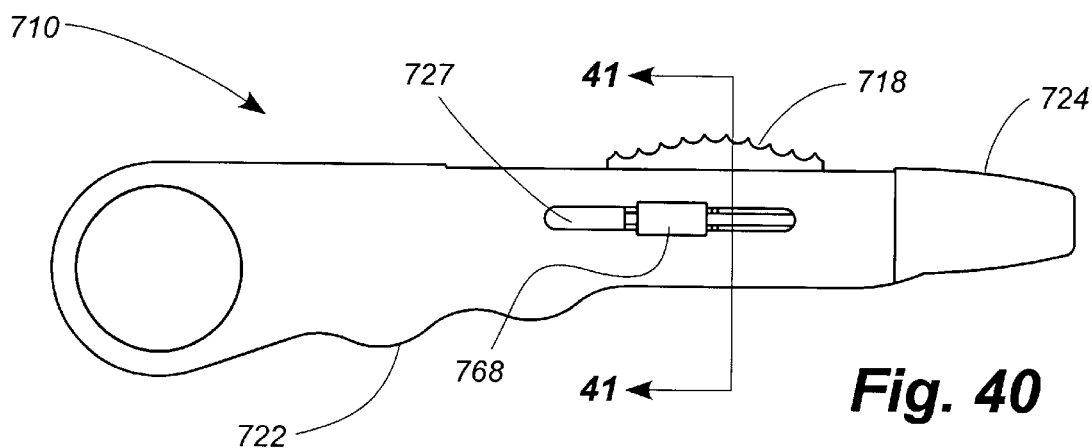
FIG. 40 is a side view of the medical retrieval device of FIG. 37.
Figure 41:
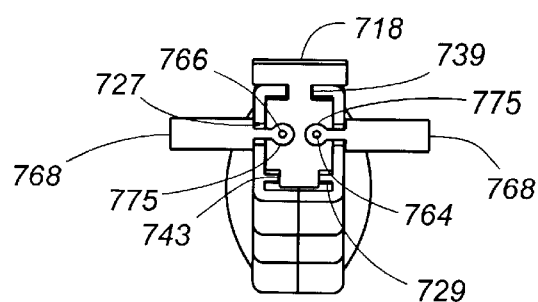
FIG. 41 is a section view taken along line 41—41 of FIG. 40.

Looking first at FIGS. 37–41, the device 710 includes a handle 712, a slide assembly 718, a sheath (not shown), and a basket (also not shown). The handle 712 comprises a handle body 720 consisting of two handle body halves 720a, 720b (FIG. 37). The handle body halves 720a, 720b are mirror images of one another, with the exception that one half 720a has guide pins and the other half 720b has corresponding holes into which the pins of the first half 720a fit.

The handle 712 further comprises a grip 722 contoured to fit the hand of the operator and formed along the lower edge of the handle body 720. A hollow nose 724 is formed at the forward end of the handle body 720. An opening 726 extends through the hollow nose 724. Each of the body halves 720a, 720b has a longitudinal slot 727. Mutually opposed, inwardly projecting longitudinal ribs 729 (FIG. 37) are formed on the inner surfaces of the body halves 720a, 720b. A longitudinal groove 731 is formed in the upper surface of the handle 712.

The slide assembly 718 comprises a body portion 735 and a button member 736 atop the body portion 735 and adapted to receive the thumb of the operator. The button member 736 includes a ribbed upper surface 738 to minimize slippage of the operator's thumb on the button member 736. A narrowed neck portion 739 connects the button member 736 to the body portion 735. A pair of longitudinally extending cylindrical recesses 741 are formed in the body portion 735 adjacent the lateral edges of the body potion 735. Recesses 743 are formed in the lower lateral edges of the body portion 735.

Like the embodiments previously described, the device 710 includes a pair of elongated tubes 764, 766 which are connected to the basket at their forward ends. The rearward ends of the tubes 764, 766 are connected to hubs 768. Each hub 768 includes a flange 769 having concave front and rear edges 771, 773 adapted to receive a finger of an operator. Each hub 768 further includes a cylindrical body portion 775 to which the tubes 764, 766 are mounted.

The device 710 will be understood to have a sheath attached to the forward end of the handle 720, like the embodiment 10 described above. Further, the tubes 764, 766 will be understood to extend through the sheath to a basket at the forward end of the sheath. The basket and sheath are not shown in FIGS. 37–44 for convenience of description.

To assemble the device 710, the tubes 764, 766 and the cylindrical portions 775 of the hubs 768 are inserted through the longitudinal slots 727 in their respective body halves 720a, 720b so that the tubes and the cylindrical portions are located on the inner side of the body halves, and the flanges 769 of the hubs 768 are located on the outer side of the body halves. The tubes 764, 766 are inserted through the opening 726 in the nose 724 and through the sheath. The cylindrical portions 775 of the hubs 768 are next inserted into the longitudinally extending cylindrical recesses 741 in the body portion 735 of the slide assembly 718. The body halves 720a, 720b are then assembled, capturing the slide assembly 718 therebetween. The neck portion 739 of the slide assembly 718 rides within the longitudinal groove 731 in the upper surface of the handle 712. The recesses 743 in the lower lateral edges of the body portion 735 ride on the inwardly projecting longitudinal ribs 729 on the inner surfaces of the body halves 720a, 720b. Thus the slide assembly 718 is freely slidable between a rearmost position defined by the rearward end of the longitudinal groove 731 and a forward position defined by the forward end of the longitudinal groove.

Figure 42:
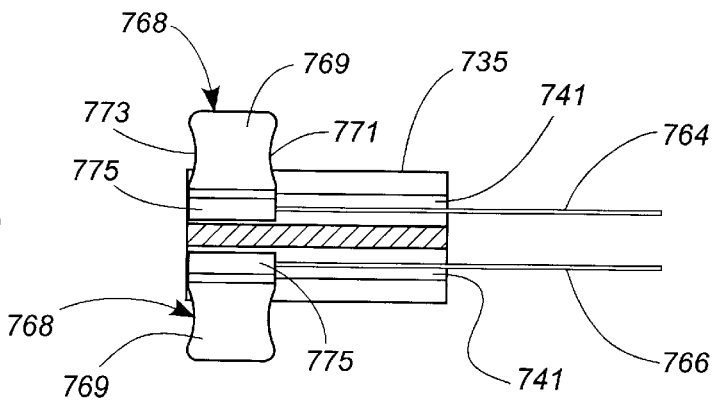
FIG. 42 is a horizontal cross-sectional view of the slide of the medical retrieval device of FIG. 37 showing the linear actuators in their retracted positions.
Figure 43:
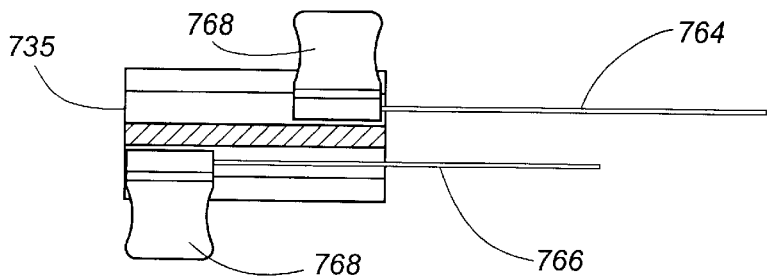
FIG. 43 is a horizontal cross-sectional view of the slide of FIG. 42 showing a first linear actuator advanced to articulate the basket in a first direction.
Figure 44:
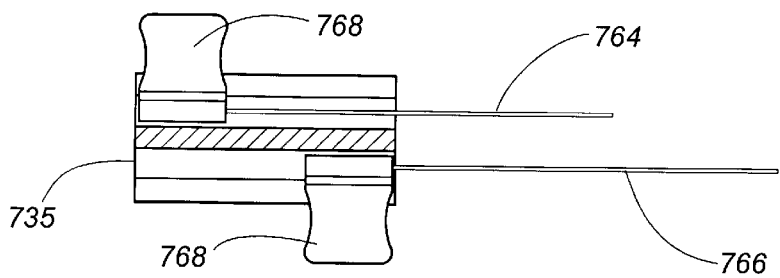
FIG. 44 is a horizontal cross-sectional view of the slide of FIG. 42 showing a second linear actuator advanced to articulate the basket in a second direction.

To use the device 710, the basket is extended and retracted by advancing or withdrawing the slide assembly 718, in the same manner explained above with respect to the device 10. When the hubs 768 are both in their rearmost positions, as shown in FIG. 42, the basket is in its normal, unarticulated position. If it is desired to articulate the basket toward the right, the left hub 768 is advanced, as shown in FIG. 43, causing the tube 764 to extend. To articulate the basket toward the left, the right hub 768 is advanced, as shown in FIG. 44, causing the tube 766 to extend.

Figure 45:
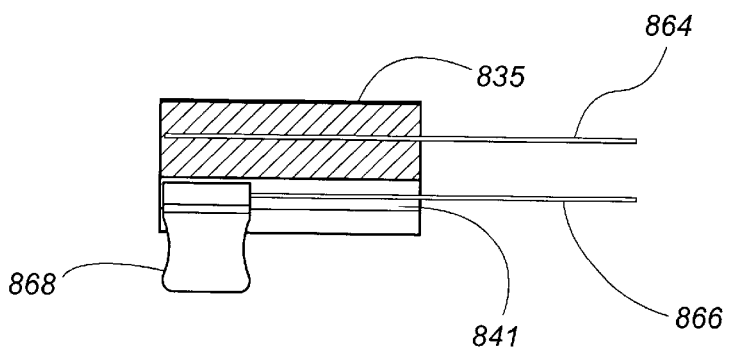
FIG. 45 depicts an alternate embodiment of a slide assembly in which the slide body has only one cylindrical recess to receive one movable tube, and the other tube is fixedly attached to the slide body.
Figure 46:
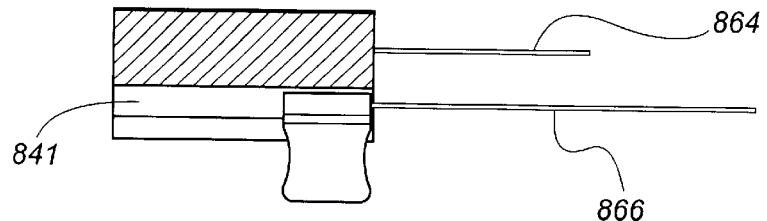
FIG. 46 illustrates the alternate embodiment of FIG. 45 with the movable tube in an advanced position.

FIGS. 45 and 46 illustrate an alternate embodiment of a slide assembly 818 for use with a handle (not shown) similar to is the handle 712 of the previously described embodiment 710. The slide assembly 818 includes a body portion 835 which will be understood to be configured similar to the body portion 735, with the exception that the body portion 835 has only a single longitudinally extending cylindrical recesses 841. The first tube 864 is fixedly attached to the body portion 835 of the slide assembly. The second tube 866 has a hub 868 connected to its rearward end. The hub 868 is slidably mounted to the body portion 835 in the same manner as previously described above with respect to hubs 768 and body portion 735. The hub 868 comprises a laterally extending flange 869. The hub 868 mounts to a handle as previously described, with the flange 869 extending through one of the slots (e.g., slots 727) in the handle. Since there is only one hub 768, the second slot in the handle can be eliminated.

To use a device with the slide assembly 818, the slide assembly is advanced or retracted to extend or withdraw the tubes 864, 866 and hence the basket attached to the forward ends of the tubes. The hub 868 is normally in its rearward position, as shown in FIG. 45. To articulate the basket, the hub 868 is advanced, as shown in FIG. 46, causing the tube 866 to advance with respect to the body portion 835 while the second tube 864 remains stationary with respect to the body portion 835.

According to this arrangement, the basket can be steered in only one direction. If desired, the "normal" position of the hub 868 can be on the lateral centerline of the body portion 835, whereby retracting the hub rearward of its normal position, to the orientation depicted in FIG. 45, will steer the basket in a first direction, and moving the hub forward of its normal position, as shown in FIG. 46, will steer the basket in the opposite direction.

Figure 47:
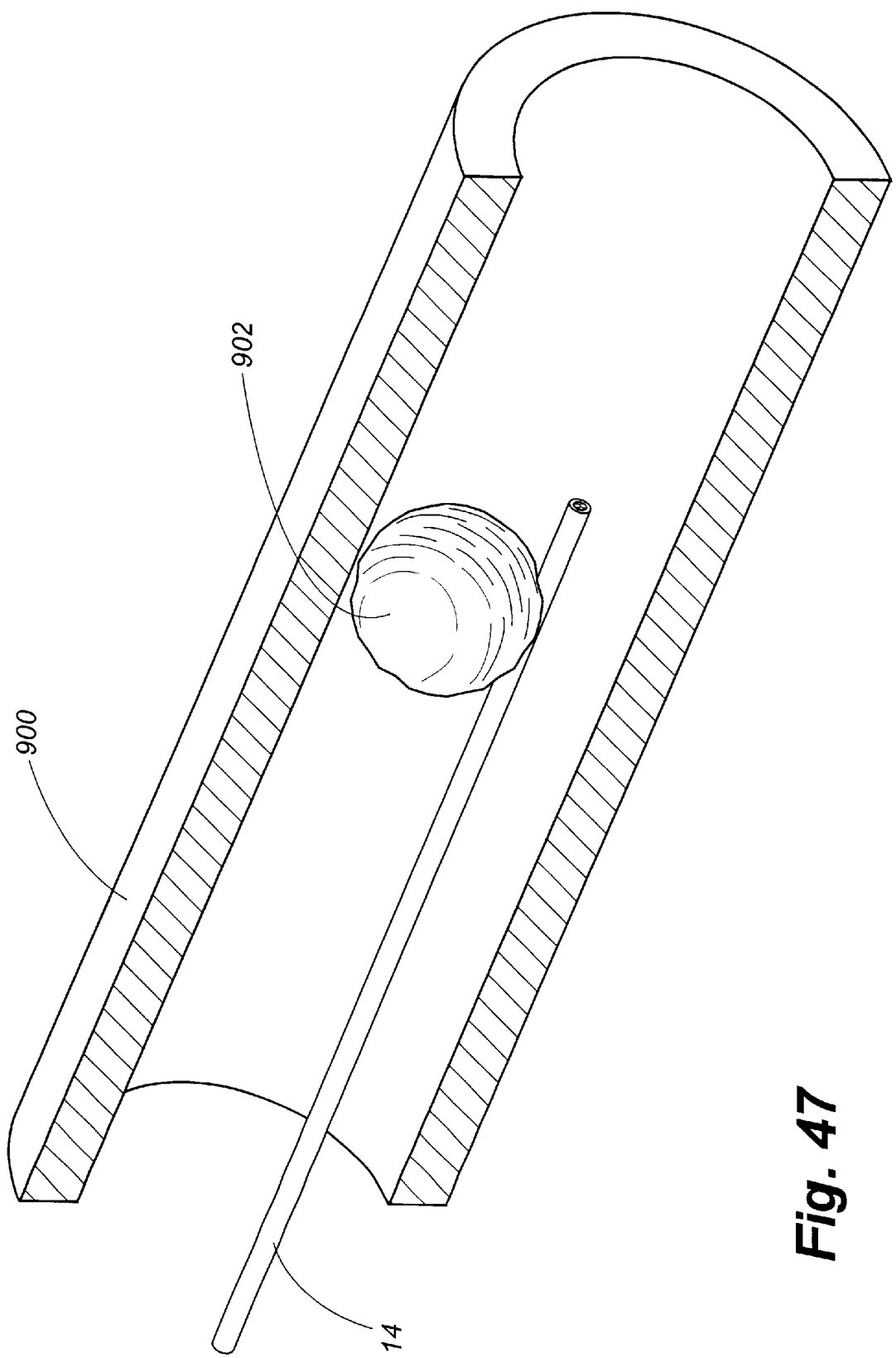
Figure 48:
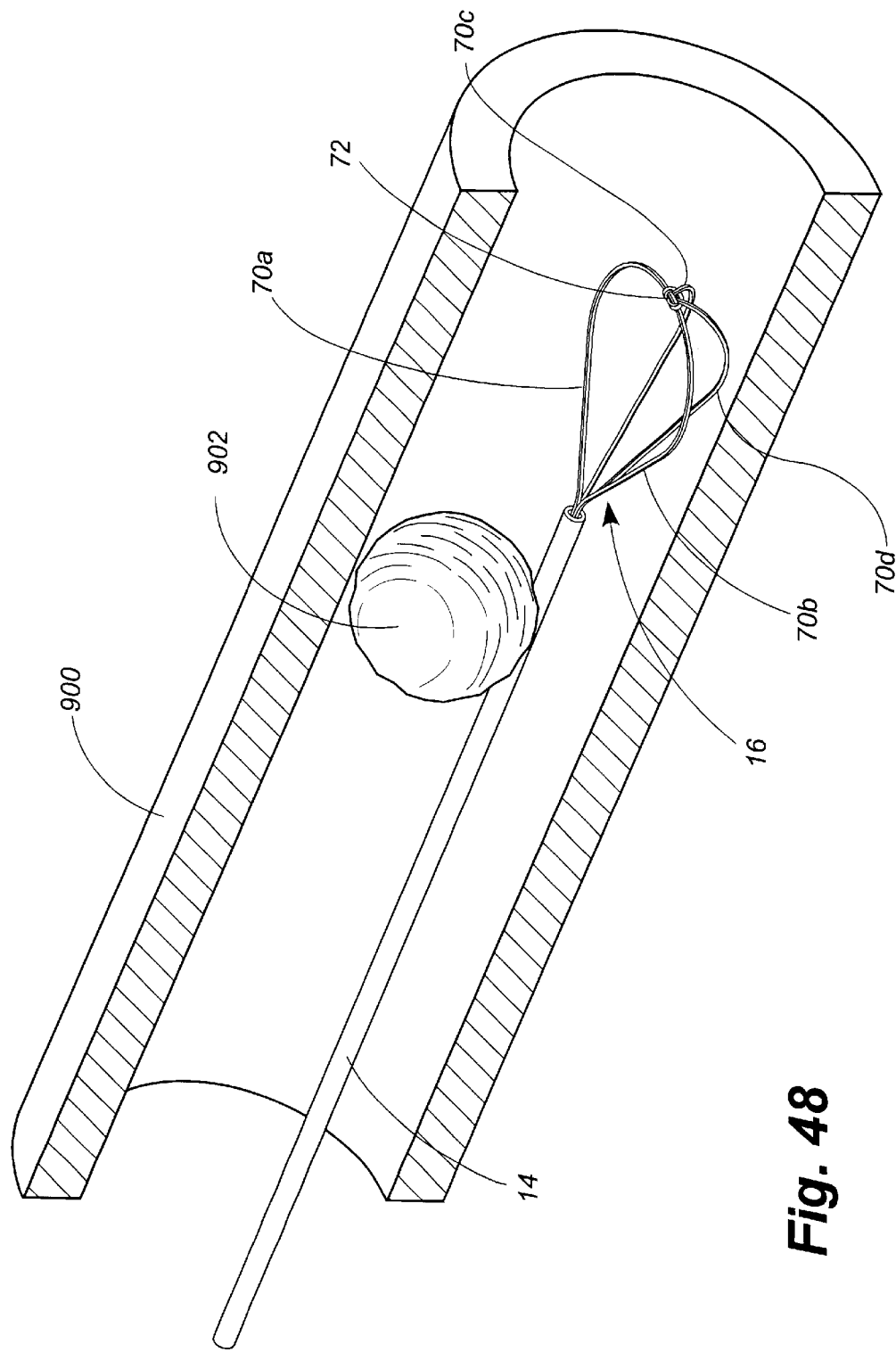
Figure 49:
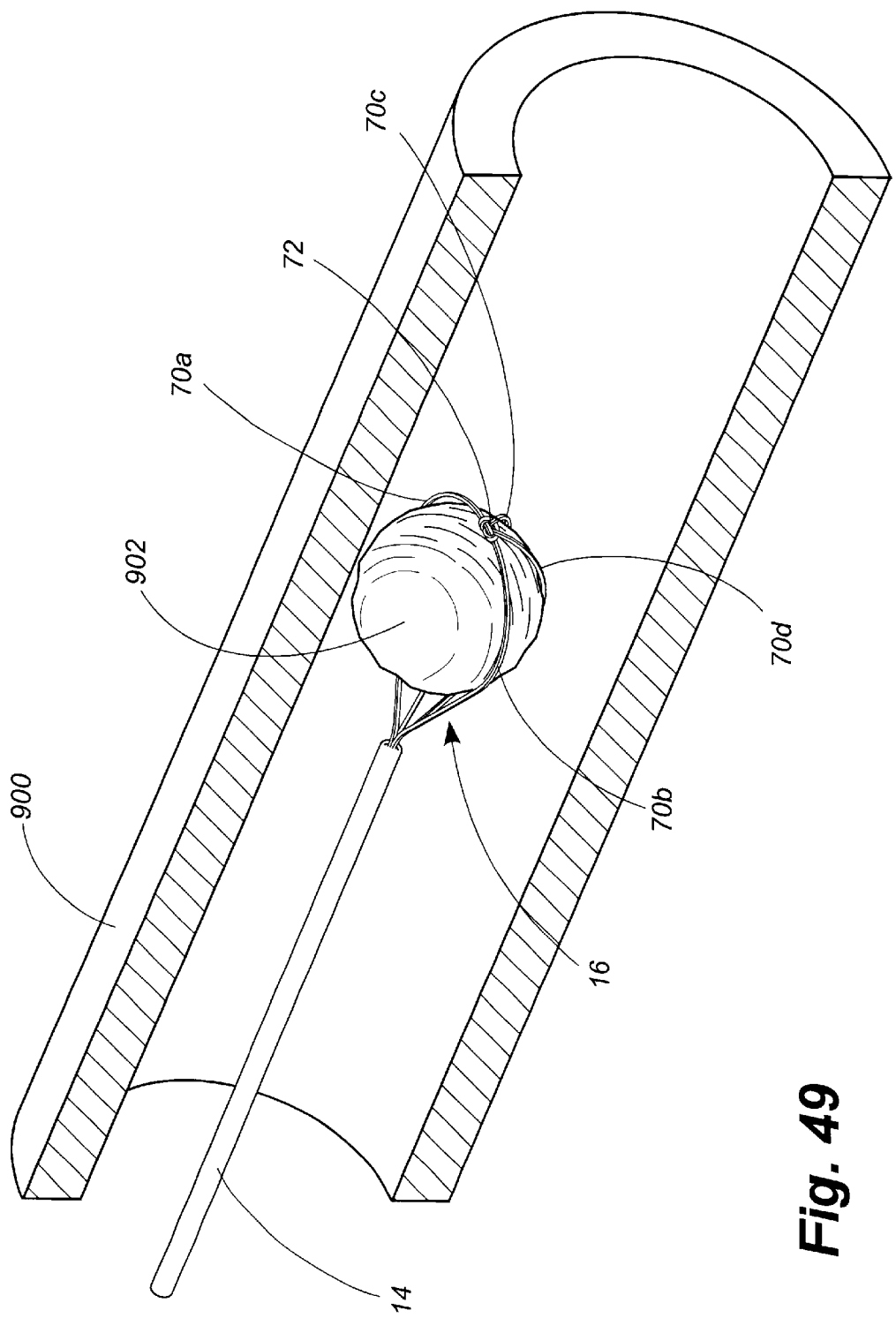

The device 10 and its variations can be used to extract a stone from the body of a patient in at least three different ways. The first way, illustrated in FIGS. 47–49, is a conventional method of using a stone basket. For purposes of example, a duct 900 such as a ureter. The forward end of the device, with the basket 16 contained within the sheath 14, is maneuvered past a stone 902, as shown in FIG. 47. The basket 16 is then deployed, as shown in FIG. 48. As the basket 16 is withdrawn back past the stone 902, as shown in FIG. 49, the stone is captured in the basket. The basket is then retracted (or the sheath advanced, depending upon the embodiment) to tighten the wires around the stone. The device with captured stone is then extracted from the patient's body.

Figure 50:
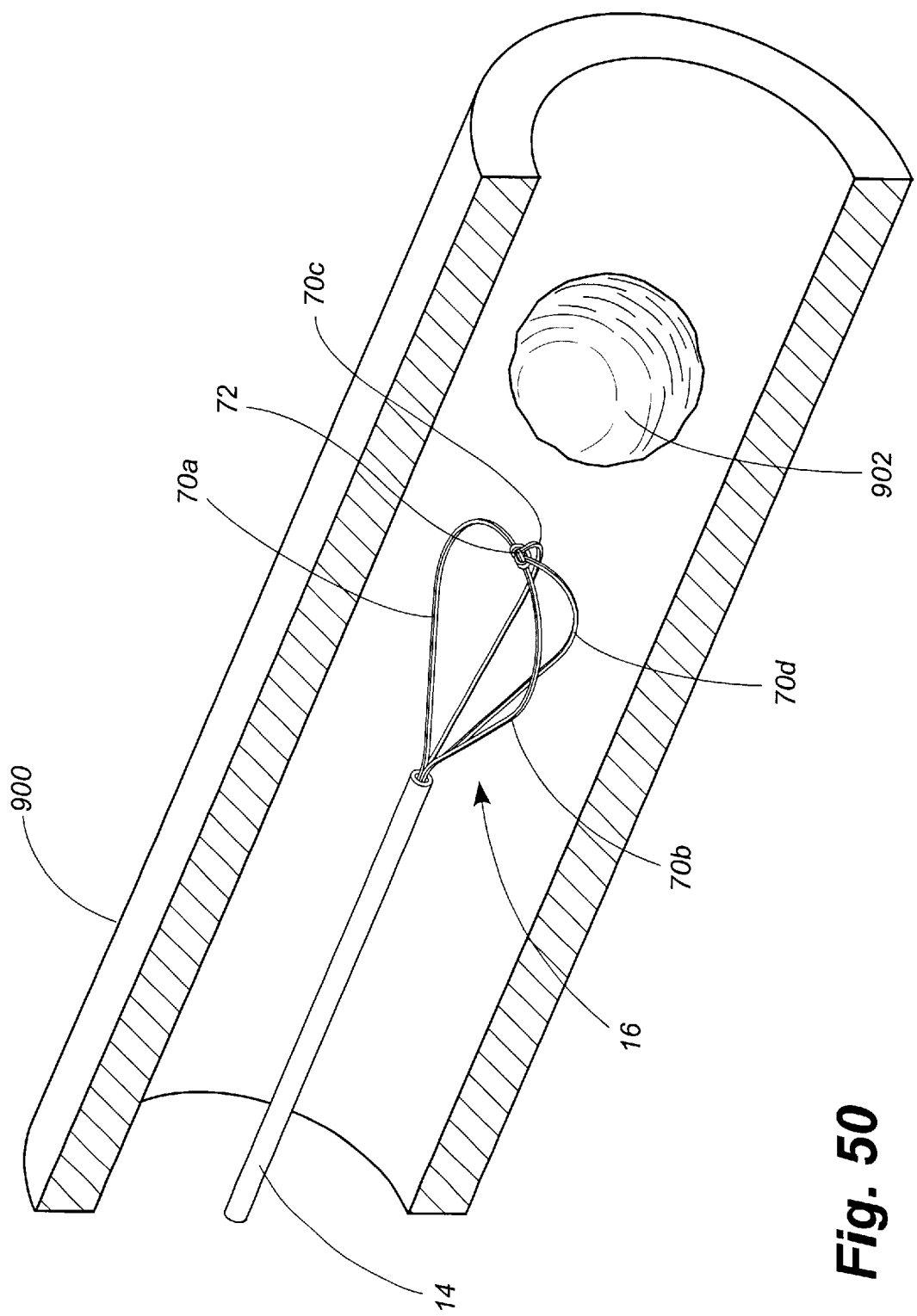
Figure 51:
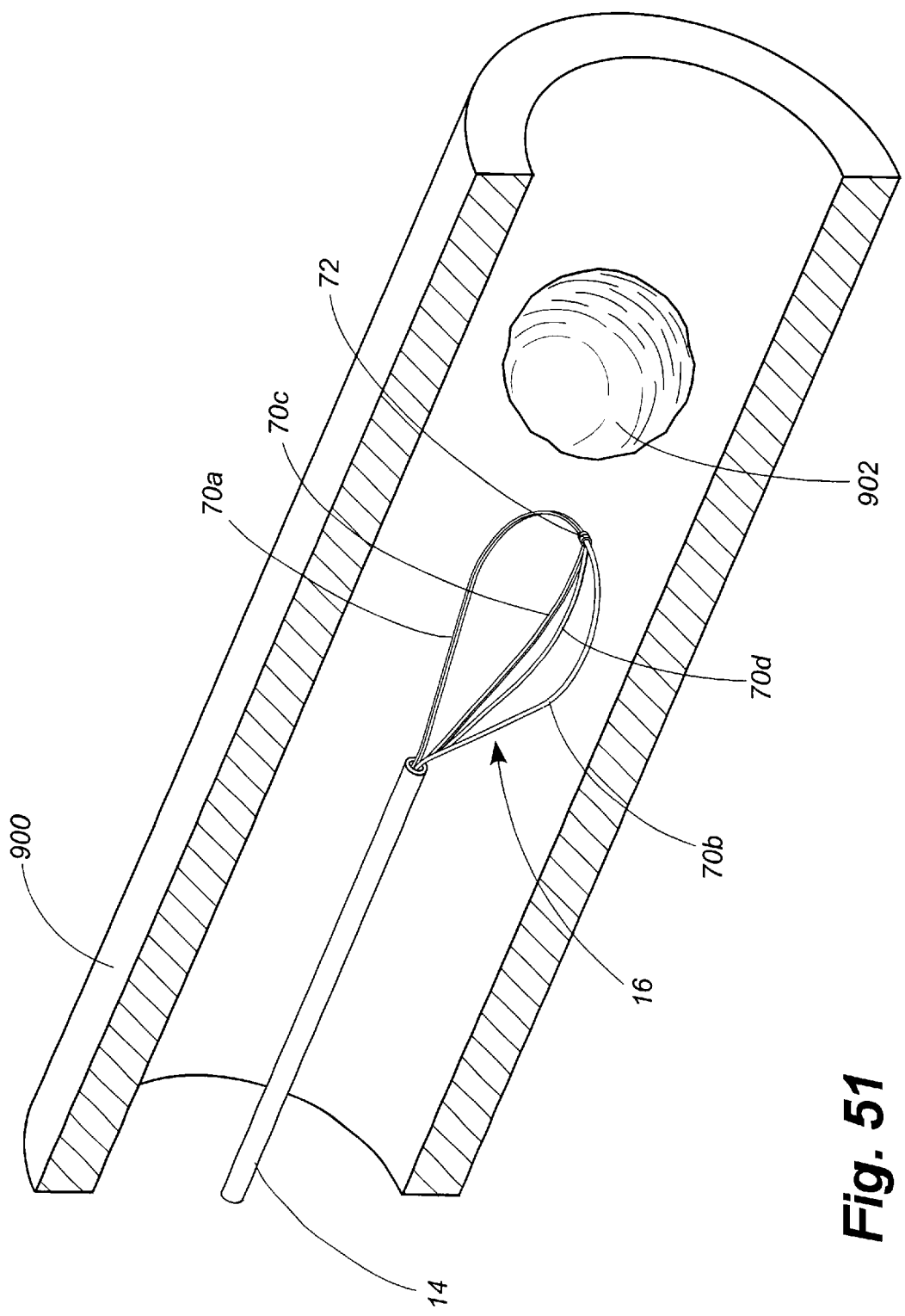
Figure 52:
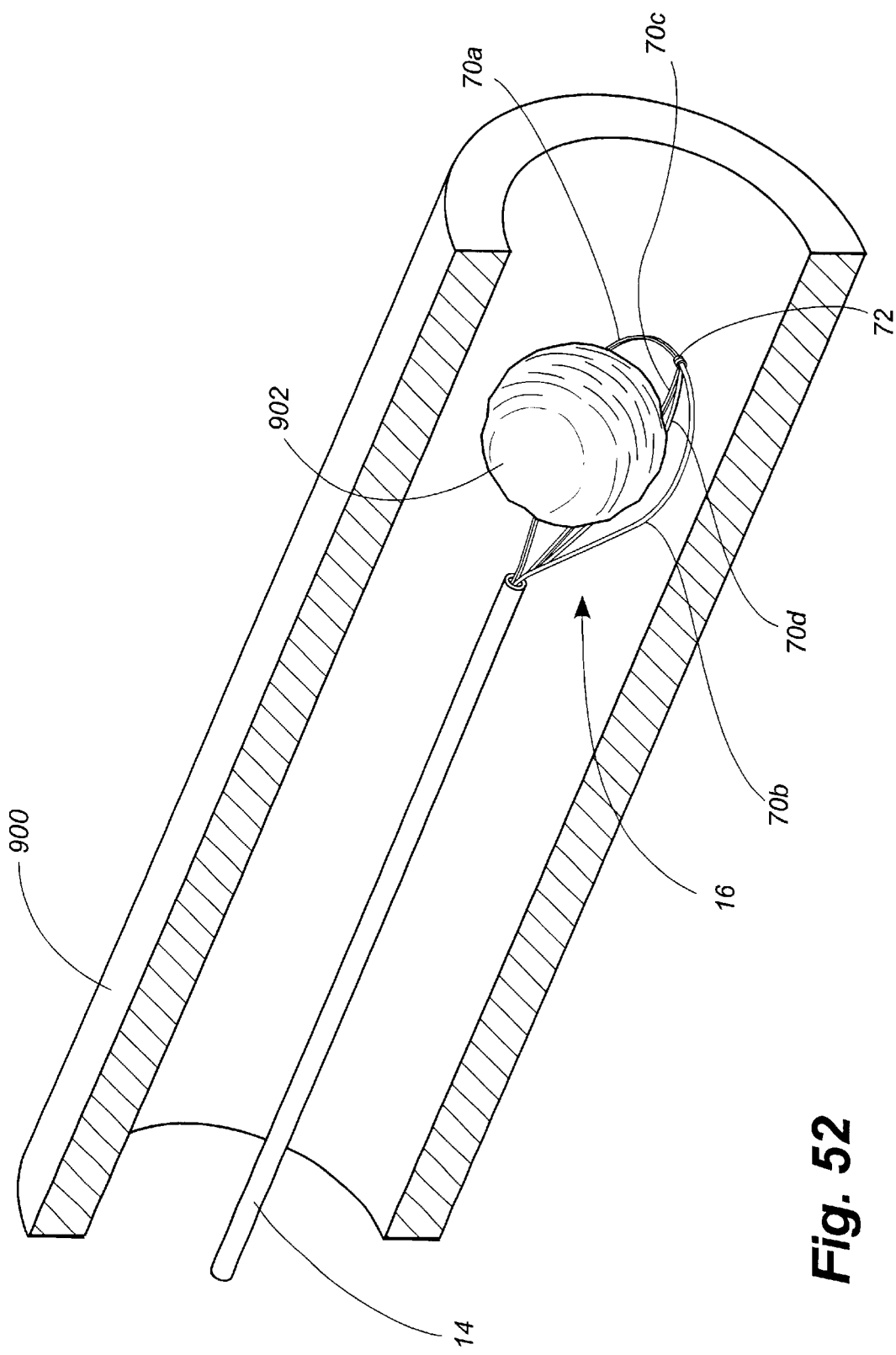
Figure 53:
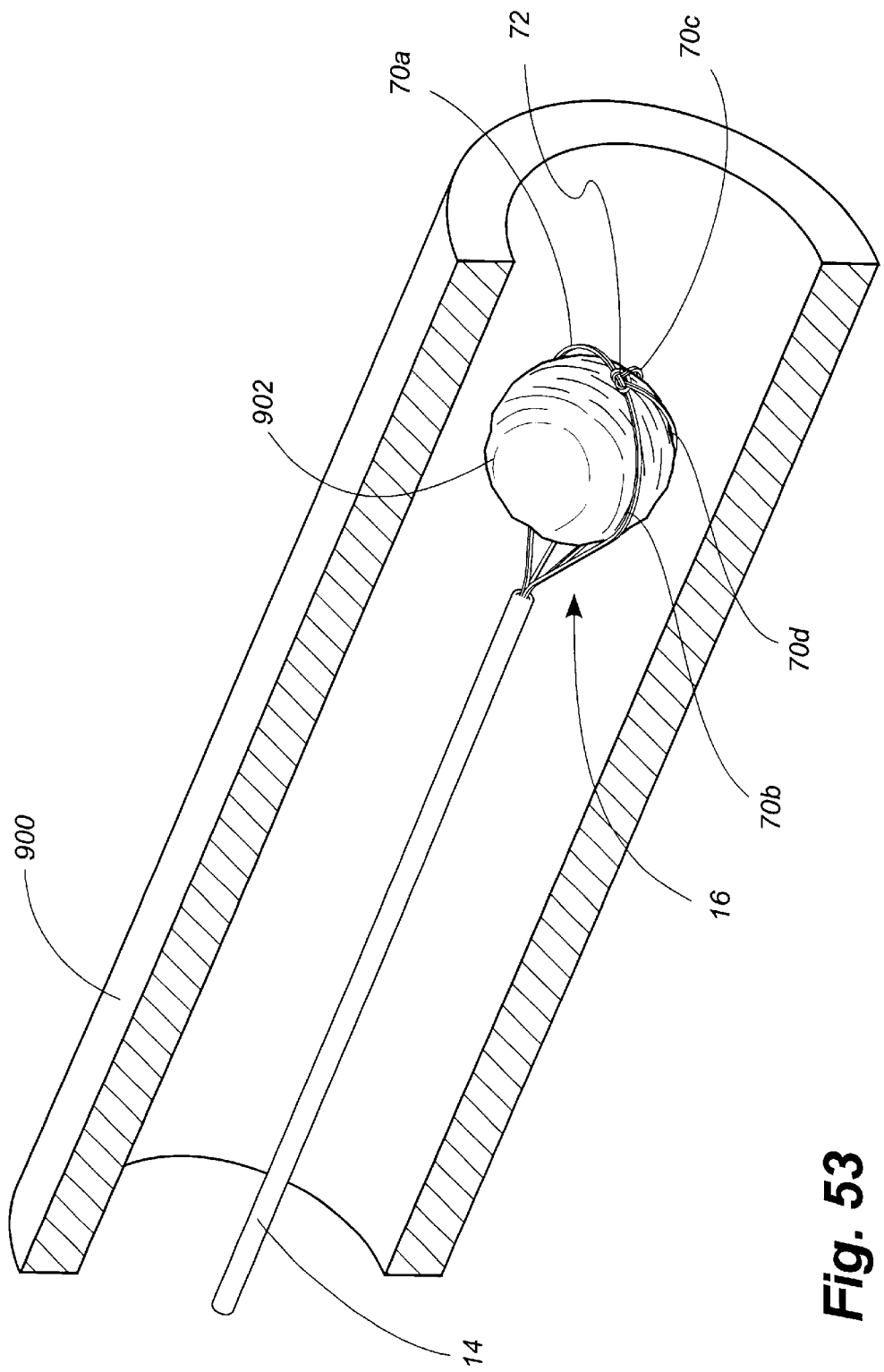

Use of the device 10 to capture a stone 902 from the body of a patient according to a second method will now be explained with reference to FIGS. 50–53. With the basket 16 retracted within the sheath 14, the forward end of the device is inserted into the patient to a location adjacent the target site. As the forward end of the device nears the stone 902, the basket 16 is opened. As shown in FIG. 50, the four basket wires 70a–70d expand. The basket 16 is then articulated downward, as shown in FIG. 51. The lower basket wires 70c, 70d retract, and the upper basket wires 70a, 70b extend, causing the basket to tip downward. The device is then advanced, the basket 16 "scooping" up the stone 902 as shown in FIG. 52. The basket is then partially retracted, as shown in FIG. 53, to tighten the basket wires 70a–70d around the stone 902.

Figure 54:
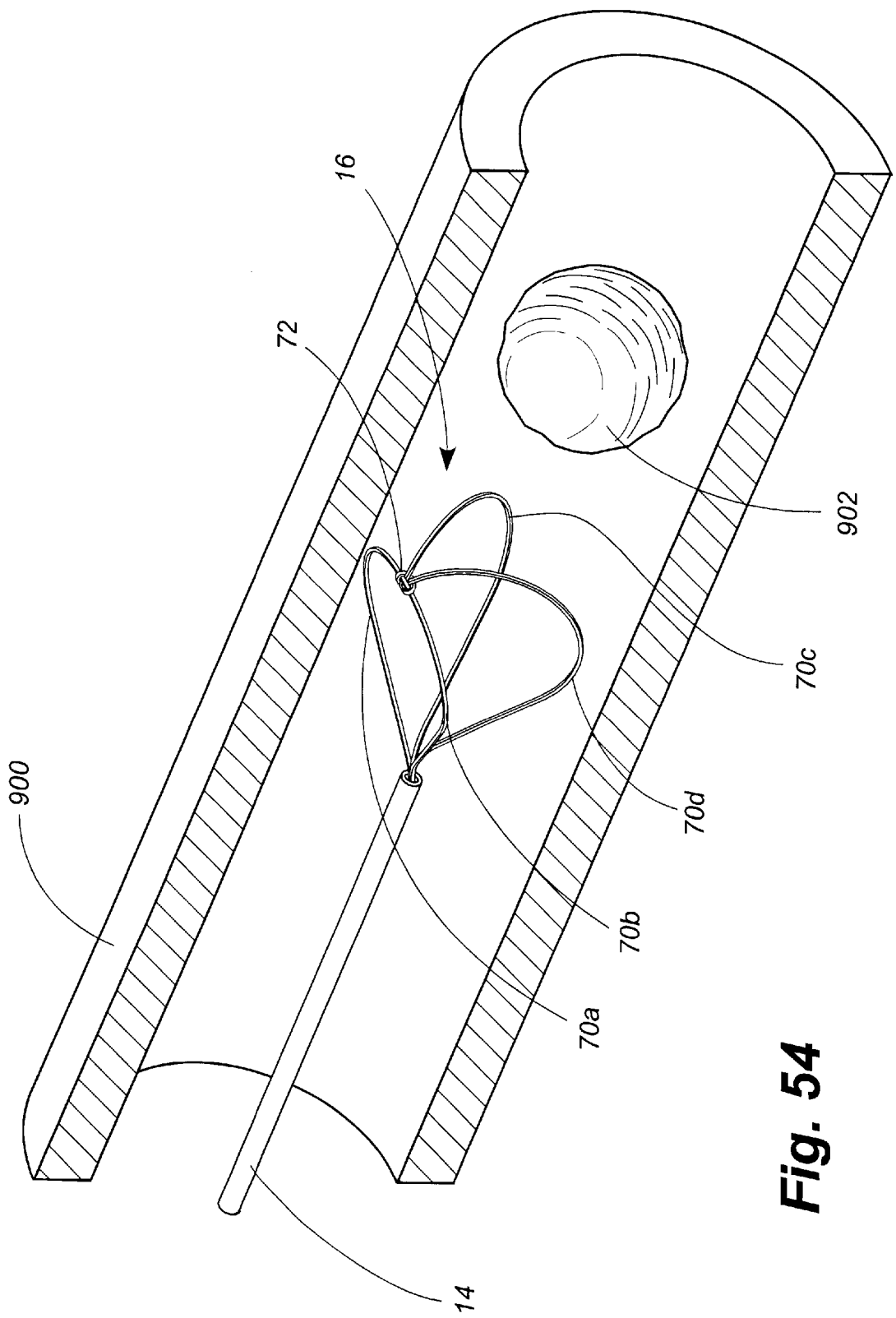
Figure 55:
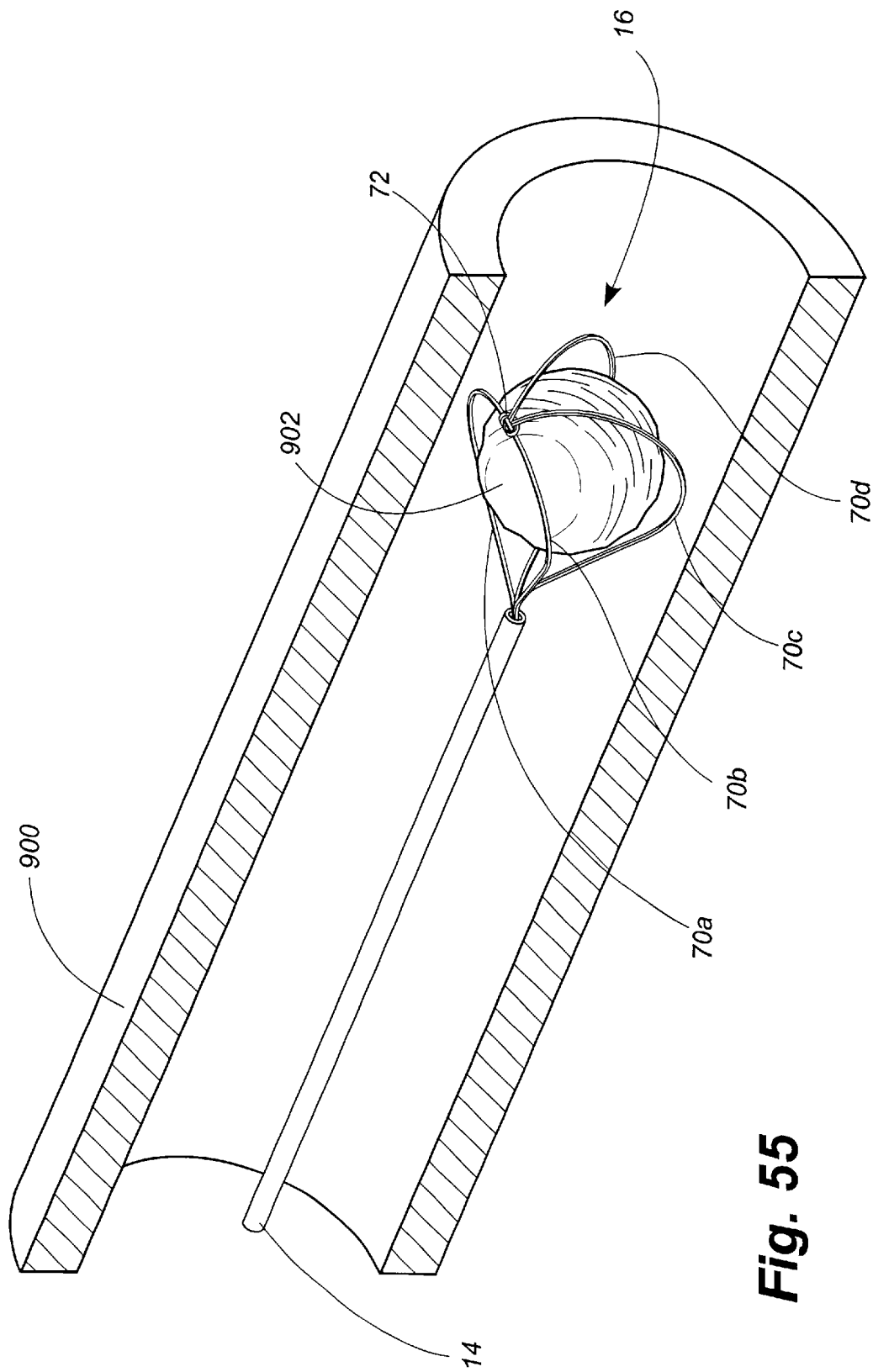

A third method for retrieving a stone 902 from the body of the patient is shown in FIGS. 54 and 55. The first step is identical to the first step of the previous method, as depicted in FIG. 50. In this expanded but unarticulated configuration, the junction 72 of the basket 16 is the forwardmost element of the device. With the basket 16 thus deployed, the device is actuated to articulate the basket upward. The lower basket wires 70c, 70d extend, and the upper basket wires 70a, 70b retract, causing the basket to tip upward, as shown in FIG. 54. This articulation causes the junction 72 to be displaced upward and rearward, such that the junction is no longer the forwardmost point of the device. In addition, articulation causes the lower two legs 70c, 70d to spread apart in clamshell fashion, thereby creating a larger opening to facilitate maneuvering the basket 16 around the stone 702.

The device is now maneuvered to the position shown in FIG. 55, where the basket 16 surrounds the stone 702. The slide is then displaced rearward to partially retract the basket 16, causing the basket legs 70a–70d to tighten around the stone 702, as previously described with respect to FIG. 53. With the stone 702 thus snared, the device is withdrawn to remove the stone from the duct 900.

In the case of larger stones whose diameter exceeds the depth of the basket 16, the basket can be articulated to retract the upper legs 70a, 70b before displacing the slide rearward. In this manner the upper legs 70a, 70b will engage the stone above its centerline, thereby providing a more secure grasp.

Finally, it will be understood that the preferred embodiment has been disclosed by way of example, and that other modifications may occur to those skilled in the art without departing from the scope and spirit of the appended claims.

What is claimed is:

1. A medical retrieval device comprising:
    a handle;
    an actuator having an axis of rotation and being mounted to said handle for rotational movement with respect thereto; and
    a basket having at least three legs, an adjacent two of said legs being connected to a first location on said actuator radially spaced apart from said axis of rotation, and the remainder of said legs being connected to a second location on said actuator radially spaced apart from said axis of rotation such that rotation of said actuator displaces said two legs in a first direction with respect to said sheath and displaces the remainder of said legs in a second direction different from said first direction.

2. The medical retrieval device of claim 1, further comprising a slide attached to said handle for longitudinal movement with respect thereto along a path between a rearward location and a forward location,
    wherein said actuator is rotatably mounted to said handle by said actuator being rotatably mounted to said slide which in turn is mounted to said handle.

3. The medical retrieval device of claim 2, further comprising:
    a hollow sheath fixedly mounted to and extending forward from said handle, said sheath having a forward end, and said basket being located at a forward end of said sheath,
    said basket being operatively associated with said slide such that said basket is retracted within a forward portion of said sheath when said slide is in said rearward location, and said basket being extended forward of said forward end of said sheath when said slide is in said forward location;
    whereby longitudinal movement of said slide extends and retracts said basket.

4. The medical retrieval device of claim 1, further comprising:
    a slide attached to said handle for longitudinal movement with respect thereto along a path between a rearward location and a forward location,
    a hollow sheath mounted to said slide and extending forward from said handle, said sheath having a forward end, and said basket being located at a forward end of said sheath,
    said sheath being operatively associated with said slide such that said sheath is retracted to expose said basket when said slide is in said rearward location, and said sheath being extended forward to cover said basket when said slide is in said forward location;
    whereby longitudinal movement of said slide extends and retracts said sheath.

5. The medical retrieval device of claim 1,
    wherein prior to said actuator being rotated, said two legs are separated by a first distance; and
    wherein when said actuator is operated to displace said two legs in a direction away from said actuator, said two legs are separated by a second distance greater than said first distance.

6. The medical retrieval device of claim 1, further comprising a wheel operatively associated with said actuator such that rotation of said wheel rotates said actuator to displace said basket legs.

7. The medical retrieval device of claim 3, further comprising a pair of tubes telescopically disposed within said sheath, a first one of said pair of tubes being connected to said first location on said actuator, and a second one of said pair of tubes being connected to said second location on said actuator, and wherein said adjacent two basket legs are connected to said first location on said actuator by said adjacent two basket legs being connected to a forward end of said first tube, and wherein said remainder of said basket legs are connected to said second location on said actuator by said remainder of said basket legs being connected to a forward end of said second tube.

8. The medical retrieval device of claim 1, wherein said actuator comprises a drum.

9. The medical retrieval device of claim 8, wherein said drum comprises a cylindrical wall, and wherein said first and second locations on said drum are located on said cylindrical wall.

10. The medical retrieval device of claim 7,
    wherein said actuator comprises a drum having a cylindrical outer wall;
    wherein said first and second locations on said drum are located on said cylindrical wall;
    wherein said drum comprises passages in said cylindrical wall at said first and second locations;
    wherein said first one of said pair of tubes is connected to said first location on said drum by a first cable having a first end connected to said first one of said pair of tubes and a second end inserted into said passage at said first location; and
    wherein said second one of said pair of tubes is connected to said second location on said drum by a second cable having a first end connected to said second one of said pair of tubes and a second end inserted into said passage at said second location.

11. The medical retrieval device of claim 8, wherein said drum comprises an end wall, and wherein said first and second locations on said drum are located on said end wall.

12. The medical retrieval device of claim 3,
    wherein said rotary actuator comprises a drum having an end wall;
    wherein said first and second locations on said drum are located on said end wall;
    wherein said drum comprises passages on said end wall at said first and second locations;
    wherein each of said pair of tubes comprises a laterally projecting pin at a rearward end thereof;
    wherein said first one of said pair of tubes is connected to said first location on said drum by said pin of said first tube being inserted into said passage at said first location; and
    wherein said second one of said pair of tubes is connected to said second location on said on said drum by said pin of said second tube being inserted into said passage at said second location.

13. The medical retrieval device of claim 3,
    wherein said rotary actuator comprises a drum having an end wall;
    wherein said first and second locations on said drum are located on said end wall;
    wherein said drum comprises pins projecting from said end wall at said first and second locations;
    wherein said first one of said pair of tubes is connected to said first location on said drum by a first hook attached to said first one of said pair of tubes and hooked to said pin at said first location; and
    wherein said second one of said pair of tubes is connected to said second location on said drum by a second hook attached to said second one of said pair of tubes and hooked to said pin at said second location.

14. A medical retrieval device comprising:
    a handle;
    a hollow sheath extending forward from said handle, said sheath having a forward end;
    a slide attached to said handle for longitudinal movement with respect thereto along a path between a rearward location and a forward location; and
    a basket located at a forward end of said sheath, said basket having at least three legs, two of said legs comprising a continuous loop lying in a plane, said ends of said loop being operatively connected to said slide, and a third leg having a forward end joined to said continuous loop at an intermediate location thereon and a rearward end being operatively connected to said slide, all of said legs of said basket are located on one side of said plane defined by said continuous loop;
    said basket being retracted within a forward portion of said sheath when said slide is in said rearward location, and said basket being extended forward of said forward end of said sheath when said slide is in said forward location, whereby longitudinal movement of said slide extends and retracts said baskets;
    wherein said basket has no legs operatively associated with it which lie on a side of said plane opposite said one side of said plane defined by said continuous loop.

15. The medical retrieval device of claim 14, wherein said basket further comprises a fourth leg, said fourth leg having a forward end joined to said continuous loop at an intermediate location thereon and a rearward end being operatively connected to said slide, and said fourth leg being located on said one side of said plane defined by said continuous loop.

16. The medical retrieval device of claim 14, wherein said loop comprises a first loop, and wherein said third and fourth legs comprise a second continuous loop, said forward ends of said third and fourth legs comprising a midpoint on said second continuous loop, and said ends of said second continuous loop being operatively connected to said slide.

17. The medical retrieval device of claim 14, wherein said first and second legs are substantially flat in cross-section, and wherein said third and fourth legs are substantially round in cross-section.

18. The medical retrieval device of claim 14, wherein said first and second legs are substantially round in cross-section, and wherein said third and fourth legs are substantially flat in cross-section.

19. The medical retrieval device of claim 16,
    further comprising an actuator means for extending said third and fourth legs with respect to said first and second legs, and
    wherein prior to said actuator means being actuated to extend said third and fourth legs with respect to said first and second legs, said third and fourth legs are separated from one another by a first distance; and
    wherein when said actuator means is actuated to extend said third and fourth legs with respect to said first and second legs, said third and fourth legs are separated from one another by a second distance greater than said first distance.

20. A method for retrieving material from a body, comprising:

inserting a medical retrieval device into a body, the device comprising a handle, a hollow sheath extending forward from said handle, said sheath having a forward end, a slide attached to said handle for longitudinal movement with respect thereto along a path between a rearward location and a forward location, a rotary actuator having an axis of rotation generally transverse to said path of movement of said slide and being mounted to said slide for rotational movement with respect thereto, and a basket located at said forward end of said sheath, said basket having at least three legs, an adjacent two of said legs being connected to a first location on said rotary actuator radially spaced apart from said axis of rotation, and the remainder of said legs being connected to a second location on said rotary actuator radially spaced apart from said axis of rotation and being on an opposite side of said axis of rotation from said first location such that rotation of said rotary actuator displaces said two legs in a first direction with respect to said sheath and displaces the remainder of said legs in a direction opposite said first direction, said basket being retracted within a forward portion of said sheath when said slide is in said rearward location, and said basket being extended forward of said forward end of said sheath when said slide is in said forward location;

longitudinally advancing said slide with respect to said handle to extend said basket;

maneuvering said basket to surround the material by rotating said rotary actuator to move at least one of said legs independently from at least one of said other legs;

longitudinally retracting said slide with respect to said handle to retract said basket to grasp the material with the legs of the basket; and withdrawing said device from the body to remove the grasped material from the body.

21. A medical retrieval device comprising:

a handle;

an actuator having an axis of rotation and being mounted to said handle for rotational movement with respect thereto; and a basket having at least three legs, an adjacent two of said legs being connected to a location on said actuator radially spaced apart from said axis of rotation such that rotation of said actuator displaces said two legs with respect to said handle, and the remainder of said legs being connected to said handle in fixed relation to said actuator.

22. The device of claim 21, further comprising:

a slide attached to said handle for longitudinal movement with respect thereto along a path between a rearward location and a forward location;

wherein said actuator being mounted to said handle for rotational movement with respect thereto comprises said actuator being mounted to said slide for rotational movement with respect thereto; and wherein the remainder of said legs being connected to said handle in fixed relation to said actuator comprises said legs being connected to said slide.

23. The device of claim 22, further comprising a hollow sheath extending forward from said handle, said sheath having a forward end; said basket being retracted within a forward portion of said sheath when said slide is in said rearward location, and said basket being extended forward of said forward end of said sheath when said slide is in said forward location.

24. The medical retrieval device of claim 23, further comprising a pair of tubes telescopically disposed within said sheath, a first one of said pair of tubes being connected to said location on said actuator, and a second one of said pair of tubes being connected to said location on said slide, and wherein said adjacent two basket legs are connected to said location on said actuator by said adjacent two basket legs being connected to a forward end of said first tube, and wherein said remainder of said basket legs are connected to said location on said slide by said remainder of said basket legs being connected to a forward end of said second tube.

25. The medical retrieval device of claim 21, further comprising a wheel operatively associated with said actuator such that rotation of said wheel rotates said actuator to displace said basket legs.

26. The medical retrieval device of claim 21, wherein said rotary actuator comprises a drum.

27. A medical retrieval device comprising:

a handle;

a slide attached to said handle for longitudinal movement with respect thereto along a path between a rearward location and a forward location;

a basket having at least three legs; and means movably mounted to said slide and operatively associated with at least one of said basket legs for effecting translational movement of said at least one of said basket legs with respect to said slide.

28. The medical retrieval device of claim 27, wherein said means movably mounted to said slide and operatively associated with at least one of said basket legs for effecting translational movement of said at least one of said basket legs with respect to said slide comprises a hub operatively associated with at least one of said basket legs and mounted to said slide for movement with respect thereto, whereby moving said hub with respect to said slide translates said at least one of said basket legs with respect to said slide.

29. The medical retrieval device of claim 27, wherein said means movably mounted to said slide and operatively associated with at least one of said basket legs for effecting translational movement of said at least one of said basket legs with respect to said slide comprises means movably mounted to said slide and operatively associated with all of said basket legs for effecting translational movement of at least one of said basket legs with respect to said slide.

30. The medical retrieval device of claim 29, wherein said means movably mounted to said slide and operatively associated with all of said basket legs for effecting translational movement of at least one of said basket legs with respect to said slide comprises a pair of hubs movably mounted to said slide, at least one of said basket legs being operatively associated with one of said pair of hubs, and the remaining legs being operatively associated with another of said hubs.

31. The medical retrieval device of claim 27, wherein basket legs other than said at least one basket leg that is operatively associated with said moving means are fixedly attached to said slide.

* * * * *